US010568317B2

(12) United States Patent
Desharnais et al.

(10) Patent No.: US 10,568,317 B2
(45) Date of Patent: Feb. 25, 2020

(54) REDUCTION OF ERYTHROCYTE SEDIMENTATION RATE

(71) Applicant: Biomatrica, Inc., San Diego, CA (US)

(72) Inventors: Joel Desharnais, San Diego, CA (US); Victoria Arendt, Palo Alto, CA (US); Margrith Mattmann, Del Mar, CA (US)

(73) Assignee: Biomatrica, Inc., San Diego, CA (US)

( * ) Notice: Subject to any disclaimer, the term of this patent is extended or adjusted under 35 U.S.C. 154(b) by 0 days.

(21) Appl. No.: 15/780,590

(22) PCT Filed: Dec. 6, 2016

(86) PCT No.: PCT/US2016/065198
§ 371 (c)(1),
(2) Date: May 31, 2018

(87) PCT Pub. No.: WO2017/100212
PCT Pub. Date: Jun. 15, 2017

(65) Prior Publication Data
US 2018/0352806 A1    Dec. 13, 2018

Related U.S. Application Data

(60) Provisional application No. 62/264,786, filed on Dec. 8, 2015.

(51) Int. Cl.
*A01N 1/02* (2006.01)
(52) U.S. Cl.
CPC .................................. *A01N 1/021* (2013.01)
(58) Field of Classification Search
None
See application file for complete search history.

(56) References Cited

U.S. PATENT DOCUMENTS

| | | |
|---|---|---|
| 3,673,158 A | 6/1972 | Reader et al. |
| 3,700,555 A | 10/1972 | Rudolph et al. |
| 4,024,548 A | 5/1977 | Alonso et al. |
| 4,040,785 A | 8/1977 | Kim et al. |
| 4,127,502 A | 11/1978 | Li Mutti et al. |
| 4,185,964 A | 1/1980 | Lancaster |
| 4,257,958 A | 3/1981 | Powell |
| 4,264,560 A | 4/1981 | Natelson |
| 4,342,740 A | 8/1982 | Narra et al. |
| 4,451,569 A | 5/1984 | Kobayashi et al. |
| 4,473,552 A | 9/1984 | Jost |
| 4,683,195 A | 7/1987 | Mullis et al. |
| 4,683,202 A | 7/1987 | Mullis |
| 4,800,159 A | 1/1989 | Mullis et al. |
| 4,801,428 A | 1/1989 | Homolko et al. |
| 4,806,343 A | 2/1989 | Carpenter et al. |
| 4,842,758 A | 6/1989 | Crutzen |
| 4,889,818 A | 12/1989 | Gelfand et al. |
| 4,891,319 A | 1/1990 | Roser |
| 4,898,813 A | 2/1990 | Albarella et al. |
| 4,933,145 A | 6/1990 | Uchida et al. |
| 4,962,020 A | 10/1990 | Tabor et al. |
| 4,962,022 A | 10/1990 | Fleming et al. |
| 4,965,188 A | 10/1990 | Mullis et al. |
| 4,978,688 A | 12/1990 | Louderback |
| 5,039,704 A | 8/1991 | Smith et al. |
| 5,047,342 A | 9/1991 | Chatterjee |
| 5,071,648 A | 12/1991 | Rosenblatt |
| 5,078,997 A | 1/1992 | Hora et al. |
| 5,079,352 A | 1/1992 | Gelfand et al. |
| 5,089,407 A | 2/1992 | Baker et al. |
| 5,096,670 A | 3/1992 | Harris et al. |
| 5,096,744 A | 3/1992 | Takei et al. |
| 5,098,893 A | 3/1992 | Franks et al. |
| 5,147,803 A | 9/1992 | Enomoto |
| 5,198,353 A | 3/1993 | Hawkins et al. |
| 5,200,399 A | 4/1993 | Wettlaufer et al. |
| 5,240,843 A | 8/1993 | Gibson et al. |
| 5,242,792 A | 9/1993 | Rudolph et al. |
| 5,270,179 A | 12/1993 | Chatterjee |
| 5,290,765 A | 3/1994 | Wettlaufer et al. |
| 5,315,505 A | 5/1994 | Pratt et al. |
| 5,351,801 A | 10/1994 | Markin et al. |
| 5,374,553 A | 12/1994 | Gelfand et al. |
| 5,397,711 A | 3/1995 | Finckh |
| 5,403,706 A | 4/1995 | Wilk et al. |
| 5,409,818 A | 4/1995 | Davey et al. |
| 5,418,141 A | 5/1995 | Zweig et al. |
| 5,428,063 A | 6/1995 | Barak et al. |

(Continued)

FOREIGN PATENT DOCUMENTS

| | | |
|---|---|---|
| CA | 1022441 A1 | 12/1977 |
| CA | 2467563 A1 | 5/2003 |

(Continued)

OTHER PUBLICATIONS

ALA-GLN(Alanyl-Glutamine) Product Catalog. Retrieved from the internet on Feb. 16, 2018, 3 pages.
Allison et al., "Effects of Drying Methods and Additives on Structure and Function of Actin: Mechanisms of Dehydration-Induced Damage and Its Inhibition," Archives of Biochemistry and Biophysics 358(1):171-181, 1998.
Alvarez-Guerra et al., Design of ionic liquids: an ecotoxicity (Vibrio fischeri) discrimination approach. Green Chem., 13:1507-1516, 2011.
Anchordoquy et al., "Frontiers in Clinical Research—Preservation of DNA," Cell Preservation Technology 5(4):180-188, 2007.
Ando et al., "PLGA Microspheres Containing Plasmid DNA: Preservation of Supercoiled DNA via Cryopreparatin and Carbohydrate Stabilization," Journ. Pharm. Sci., 88(1):126-130, 1999.
Anonymous, "Transmucosal polymeric molecular delivery systems," retrieved from http://www.antiagingresearch.com/hgh/transmucosal.php on Apr. 7, 2005, 2 pages.

(Continued)

*Primary Examiner* — Heidi Reese
(74) *Attorney, Agent, or Firm* — Casimir Jones, S.C.; Peter J. Schlueter

(57) ABSTRACT

The present invention relates to reduction of erythrocyte sedimentation rate in a blood sample. In particular, formulations, compositions, articles of manufacture, kits and methods for reduced erythrocyte sedimentation rate in a blood sample are provided.

15 Claims, 5 Drawing Sheets

(56) References Cited

U.S. PATENT DOCUMENTS

| | | |
|---|---|---|
| 5,436,149 A | 7/1995 | Barnes |
| 5,455,166 A | 10/1995 | Walker |
| 5,496,562 A | 3/1996 | Burgoyne |
| 5,498,523 A | 3/1996 | Tabor et al. |
| 5,512,462 A | 4/1996 | Cheng |
| 5,516,644 A | 5/1996 | Yamauchi et al. |
| 5,529,166 A | 6/1996 | Markin et al. |
| 5,541,290 A | 7/1996 | Harbeson et al. |
| 5,556,771 A | 9/1996 | Shen et al. |
| 5,593,824 A | 1/1997 | Treml et al. |
| 5,614,365 A | 3/1997 | Tabor et al. |
| 5,614,387 A | 3/1997 | Shen et al. |
| 5,677,124 A | 10/1997 | Dubois et al. |
| 5,684,045 A | 11/1997 | Smith et al. |
| 5,688,516 A | 11/1997 | Raad et al. |
| 5,705,366 A | 1/1998 | Backus |
| 5,728,822 A | 3/1998 | Macfarlane |
| 5,741,462 A | 4/1998 | Nova et al. |
| 5,751,629 A | 5/1998 | Nova et al. |
| 5,763,157 A | 6/1998 | Treml et al. |
| 5,777,099 A | 7/1998 | Mehra |
| 5,777,303 A | 7/1998 | Berney |
| 5,779,983 A | 7/1998 | Dufresne et al. |
| 5,789,172 A | 8/1998 | Still et al. |
| 5,789,414 A | 8/1998 | Lapidot et al. |
| 5,798,035 A | 8/1998 | Kirk et al. |
| 5,814,502 A | 9/1998 | Hoeltke et al. |
| 5,827,874 A | 10/1998 | Meyer et al. |
| 5,834,254 A | 11/1998 | Shen et al. |
| 5,837,546 A | 11/1998 | Allen et al. |
| 5,849,517 A | 12/1998 | Ryan |
| 5,856,102 A | 1/1999 | Bierke-Nelson et al. |
| 5,861,251 A | 1/1999 | Park et al. |
| 5,863,799 A | 1/1999 | Hengstenberg |
| 5,874,214 A | 2/1999 | Nova et al. |
| 5,876,992 A | 3/1999 | De Rosier et al. |
| 5,914,272 A | 6/1999 | Dufresne et al. |
| 5,918,273 A | 6/1999 | Horn |
| 5,939,259 A | 8/1999 | Harvey et al. |
| 5,945,515 A | 8/1999 | Chomczynski |
| 5,948,614 A | 9/1999 | Chatterjee |
| 5,955,448 A | 9/1999 | Colaco et al. |
| 5,985,214 A | 11/1999 | Stylli et al. |
| 5,991,729 A | 11/1999 | Barry et al. |
| 6,013,488 A | 1/2000 | Hayashizaki |
| 6,015,668 A | 1/2000 | Hughes et al. |
| 6,017,496 A | 1/2000 | Nova et al. |
| 6,025,129 A | 2/2000 | Nova et al. |
| 6,037,168 A | 3/2000 | Brown |
| 6,050,956 A | 4/2000 | Ikegami et al. |
| 6,057,117 A | 5/2000 | Harrison et al. |
| 6,057,159 A | 5/2000 | Lepre |
| 6,071,428 A | 6/2000 | Franks et al. |
| 6,077,235 A | 6/2000 | Serpentino et al. |
| 6,090,925 A | 7/2000 | Woiszwillo et al. |
| 6,124,089 A | 9/2000 | Ryan |
| 6,127,155 A | 10/2000 | Gelfand et al. |
| 6,143,817 A | 11/2000 | Hallam et al. |
| 6,153,412 A | 11/2000 | Park et al. |
| 6,153,618 A | 11/2000 | Schultz et al. |
| 6,156,345 A | 12/2000 | Chudzik et al. |
| 6,166,117 A | 12/2000 | Miyazaki |
| 6,168,922 B1 | 1/2001 | Harvey et al. |
| 6,197,229 B1 | 3/2001 | Ando et al. |
| 6,204,375 B1 | 3/2001 | Lader |
| 6,221,599 B1 | 4/2001 | Hayashizaki |
| 6,242,235 B1 | 6/2001 | Shultz et al. |
| 6,251,599 B1 | 6/2001 | Chen et al. |
| 6,258,930 B1 | 7/2001 | Gauch et al. |
| 6,284,459 B1 | 9/2001 | Nova et al. |
| 6,294,203 B1 | 9/2001 | Burgoyne |
| 6,294,338 B1 | 9/2001 | Nunomura |
| 6,310,060 B1 | 10/2001 | Barrett et al. |
| 6,313,102 B1 | 11/2001 | Colaco et al. |
| 6,322,983 B1 | 11/2001 | Burgoyne |
| 6,323,039 B1 | 11/2001 | Dykens et al. |
| 6,329,139 B1 | 12/2001 | Nova et al. |
| 6,331,273 B1 | 12/2001 | Nova et al. |
| 6,352,854 B1 | 3/2002 | Nova et al. |
| 6,366,440 B1 | 4/2002 | Kung |
| 6,372,428 B1 | 4/2002 | Nova et al. |
| 6,372,437 B2 | 4/2002 | Hayashizaki |
| 6,380,858 B1 | 4/2002 | Yarin et al. |
| 6,416,714 B1 | 7/2002 | Nova et al. |
| 6,417,185 B1 | 7/2002 | Goff et al. |
| 6,426,210 B1 | 7/2002 | Franks et al. |
| 6,440,966 B1 | 8/2002 | Barrett et al. |
| 6,447,726 B1 | 9/2002 | Delucas et al. |
| 6,447,804 B1 | 9/2002 | Burgoyne |
| 6,448,245 B1 | 9/2002 | Depetrillo et al. |
| RE37,872 E | 10/2002 | Franks et al. |
| 6,458,556 B1 | 10/2002 | Hayashizaki |
| 6,465,231 B2 | 10/2002 | Harrison et al. |
| 6,475,716 B1 | 11/2002 | Seki |
| 6,489,344 B1 | 12/2002 | Nuss et al. |
| 6,503,411 B1 | 1/2003 | Franks et al. |
| 6,503,702 B1 | 1/2003 | Stewart |
| 6,528,309 B2 | 3/2003 | Levine |
| 6,534,483 B1 | 3/2003 | Bruno et al. |
| 6,535,129 B1 | 3/2003 | Petrick |
| 6,602,718 B1 | 8/2003 | Augello et al. |
| 6,608,632 B2 | 8/2003 | Daly et al. |
| 6,610,531 B1 | 8/2003 | Mateczun et al. |
| 6,617,170 B2 | 9/2003 | Augello et al. |
| 6,627,226 B2 | 9/2003 | Burgoyne et al. |
| 6,627,398 B1 | 9/2003 | Wilusz et al. |
| 6,638,945 B1 | 10/2003 | Gibson |
| 6,645,717 B1 | 11/2003 | Smith et al. |
| 6,649,406 B1 | 11/2003 | Williams et al. |
| 6,653,062 B1 | 11/2003 | DePablo et al. |
| 6,664,099 B1 | 12/2003 | Worrall |
| 6,667,167 B1 | 12/2003 | Sorensen et al. |
| 6,682,730 B2 | 1/2004 | Mickle et al. |
| 6,689,343 B1 | 2/2004 | Allred et al. |
| 6,689,353 B1 | 2/2004 | Wang et al. |
| 6,696,028 B2 | 2/2004 | Bara |
| 6,746,841 B1 | 6/2004 | Fomovskaia et al. |
| 6,746,851 B1 | 6/2004 | Tseung et al. |
| 6,750,059 B1 | 6/2004 | Blakesley et al. |
| 6,776,959 B1 | 8/2004 | Helftenbein |
| 6,787,305 B1 | 9/2004 | Li et al. |
| 6,800,632 B2 | 10/2004 | Nuss et al. |
| 6,803,200 B2 | 10/2004 | Xia et al. |
| 6,821,479 B1 | 11/2004 | Smith et al. |
| 6,821,789 B2 | 11/2004 | Augello et al. |
| 6,852,833 B1 | 2/2005 | Machida et al. |
| 6,858,634 B2 | 2/2005 | Asrar et al. |
| 6,861,213 B2 | 3/2005 | Oelmuller et al. |
| 6,862,789 B1 | 3/2005 | Hering et al. |
| 6,872,357 B1 | 3/2005 | Bronshtein et al. |
| 6,896,894 B2 | 5/2005 | Brody et al. |
| 6,919,172 B2 | 7/2005 | DePablo et al. |
| 6,942,964 B1 | 9/2005 | Ward et al. |
| 6,949,544 B2 | 9/2005 | Bethiel et al. |
| 6,949,547 B2 | 9/2005 | Nuss et al. |
| 7,001,770 B1 | 2/2006 | Atencio et al. |
| 7,001,905 B2 | 2/2006 | Biwersi et al. |
| 7,011,825 B2 | 3/2006 | Yamazaki et al. |
| 7,037,918 B2 | 5/2006 | Nuss et al. |
| 7,045,519 B2 | 5/2006 | Nuss et al. |
| 7,049,065 B2 | 5/2006 | Hayashizaki |
| 7,083,106 B2 | 8/2006 | Albany |
| 7,098,033 B2 | 8/2006 | Chen et al. |
| 7,101,693 B2 | 9/2006 | Cicerone et al. |
| 7,129,242 B2 | 10/2006 | Satoh et al. |
| 7,142,987 B2 | 11/2006 | Eggers |
| 7,150,980 B1 | 12/2006 | Lapidot et al. |
| 7,169,584 B2 | 1/2007 | Ward et al. |
| 7,169,816 B2 | 1/2007 | Barrett et al. |
| RE39,497 E | 2/2007 | Franks et al. |
| 7,172,999 B2 | 2/2007 | Mattern et al. |
| 7,258,873 B2 | 8/2007 | Truong-Le et al. |
| 7,270,953 B2 | 9/2007 | Hollaender et al. |
| 7,282,371 B2 | 10/2007 | Helftenbein |

(56) References Cited

U.S. PATENT DOCUMENTS

| | | |
|---|---|---|
| 7,326,418 B2 | 2/2008 | Franzoso et al. |
| 7,384,603 B2 | 6/2008 | Klein et al. |
| 7,425,557 B2 | 9/2008 | Nuss et al. |
| 7,476,754 B2 | 1/2009 | Herradon Garcia et al. |
| 7,521,460 B2 | 4/2009 | Langham et al. |
| 7,592,455 B2 | 9/2009 | Brookings et al. |
| 7,728,013 B2 | 6/2010 | Blatt et al. |
| 7,745,663 B2 | 6/2010 | Isshiki et al. |
| 7,795,256 B2 | 9/2010 | Alexander et al. |
| 7,803,839 B2 | 9/2010 | Aay et al. |
| 7,846,703 B2 | 12/2010 | Kobayashi et al. |
| 7,897,624 B2 | 3/2011 | Yan et al. |
| 7,919,294 B2 | 4/2011 | Franco De Sarabia Rosado et al. |
| 7,932,266 B2 | 4/2011 | Garcia et al. |
| 7,972,828 B2 | 7/2011 | Ward et al. |
| 8,143,271 B2 | 3/2012 | Ibrahim et al. |
| RE43,389 E | 5/2012 | Helftenbein |
| 8,178,555 B2 | 5/2012 | Chang et al. |
| 8,378,108 B2 | 2/2013 | Corkey et al. |
| 8,394,822 B2 | 3/2013 | Hutchings et al. |
| 8,440,665 B2 | 5/2013 | Corkey et al. |
| 8,492,427 B2 | 7/2013 | Gancia et al. |
| 8,519,125 B2 | 8/2013 | Whitney et al. |
| 8,530,480 B2 | 9/2013 | Kamenecka et al. |
| 8,598,360 B2 | 12/2013 | Corkey et al. |
| 8,642,584 B2 | 2/2014 | Aftab et al. |
| 8,664,244 B2 | 3/2014 | Chen |
| 8,827,874 B2 | 9/2014 | Nishimura |
| 8,900,856 B2 | 12/2014 | Muller-Cohn et al. |
| 9,078,426 B2 | 7/2015 | Muller-Cohn et al. |
| 9,376,709 B2 | 6/2016 | Whitney et al. |
| 9,725,703 B2 | 8/2017 | Whitney et al. |
| 9,845,489 B2 | 12/2017 | Whitney et al. |
| 2001/0038858 A1 | 11/2001 | Roser et al. |
| 2002/0039771 A1 | 4/2002 | Peters et al. |
| 2002/0055118 A1 | 5/2002 | Eym |
| 2002/0076819 A1 | 6/2002 | Bowman et al. |
| 2002/0081565 A1 | 6/2002 | Barnea et al. |
| 2002/0094533 A1 | 7/2002 | Hess et al. |
| 2002/0103086 A1 | 8/2002 | Asrar et al. |
| 2002/0182258 A1 | 12/2002 | Lunsford et al. |
| 2002/0197628 A1 | 12/2002 | Stewart |
| 2003/0022148 A1 | 1/2003 | Seki |
| 2003/0031697 A1 | 2/2003 | Chudzik et al. |
| 2003/0032147 A1 | 2/2003 | Sauer et al. |
| 2003/0059468 A1 | 3/2003 | Mattern et al. |
| 2003/0091971 A1 | 5/2003 | Xia et al. |
| 2003/0119042 A1 | 6/2003 | Franco De Sarabia Rosado et al. |
| 2003/0129755 A1 | 7/2003 | Sadler et al. |
| 2003/0138805 A1 | 7/2003 | Loffert et al. |
| 2003/0157088 A1 | 8/2003 | Elliott et al. |
| 2003/0162284 A1 | 8/2003 | Dordick et al. |
| 2003/0163608 A1 | 8/2003 | Tiwary et al. |
| 2003/0165482 A1 | 9/2003 | Rolland et al. |
| 2003/0175232 A1 | 9/2003 | Elliott et al. |
| 2003/0199446 A1 | 10/2003 | Bunger et al. |
| 2003/0215369 A1 | 11/2003 | Eggers et al. |
| 2004/0014068 A1 | 1/2004 | Burgoyne |
| 2004/0058349 A1 | 3/2004 | Van Ness et al. |
| 2004/0101966 A1 | 5/2004 | Davis et al. |
| 2004/0110267 A1 | 6/2004 | Sundar |
| 2004/0121420 A1 | 6/2004 | Smith |
| 2004/0121432 A1 | 6/2004 | Klein et al. |
| 2004/0137417 A1 | 7/2004 | Ryan |
| 2004/0142475 A1 | 7/2004 | Barman et al. |
| 2004/0208792 A1 | 10/2004 | Linton et al. |
| 2004/0228794 A1 | 11/2004 | Weller et al. |
| 2004/0241713 A1 | 12/2004 | Mirzabekov et al. |
| 2005/0026181 A1 | 2/2005 | Davis et al. |
| 2005/0053911 A1 | 3/2005 | Greener et al. |
| 2005/0084481 A1 | 4/2005 | Hand et al. |
| 2005/0086822 A1 | 4/2005 | Frisner et al. |
| 2005/0090009 A1 | 4/2005 | Cormier et al. |
| 2005/0112610 A1 | 5/2005 | Lee et al. |
| 2005/0124965 A1 | 6/2005 | Haywood |
| 2005/0186254 A1 | 8/2005 | Roser et al. |
| 2005/0196824 A1 | 9/2005 | Fisher et al. |
| 2005/0227269 A1 | 10/2005 | Lloyd et al. |
| 2005/0251501 A1 | 11/2005 | Phillips et al. |
| 2005/0266031 A1 | 12/2005 | Dickerson et al. |
| 2005/0276728 A1 | 12/2005 | Muller-Cohn et al. |
| 2006/0014177 A1 | 1/2006 | Hogan et al. |
| 2006/0099567 A1 | 5/2006 | Muller-Cohn et al. |
| 2006/0127415 A1 | 6/2006 | Mayeresse |
| 2006/0147944 A1 | 7/2006 | Chomczynski |
| 2006/0177855 A1 | 8/2006 | Utermohlen et al. |
| 2006/0183687 A1 | 8/2006 | Cory et al. |
| 2006/0193968 A1 | 8/2006 | Keogh et al. |
| 2006/0198891 A1 | 9/2006 | Ravenelle et al. |
| 2006/0210429 A1 | 9/2006 | Hunsley et al. |
| 2006/0293212 A1 | 12/2006 | Griese et al. |
| 2007/0020289 A1 | 1/2007 | Mattern et al. |
| 2007/0043216 A1 | 2/2007 | Bair et al. |
| 2007/0048726 A1 | 3/2007 | Baust et al. |
| 2007/0073039 A1 | 3/2007 | Chisari |
| 2007/0117173 A1 | 5/2007 | Levison et al. |
| 2007/0135528 A1 | 6/2007 | Butler et al. |
| 2007/0212760 A1 | 9/2007 | Lapidot et al. |
| 2007/0243178 A1 | 10/2007 | Ho et al. |
| 2008/0050737 A1 | 2/2008 | Arieli et al. |
| 2008/0064071 A1 | 3/2008 | Hogrefe et al. |
| 2008/0146790 A1 | 6/2008 | Grolz et al. |
| 2008/0176209 A1 | 7/2008 | Muller et al. |
| 2008/0187924 A1 | 8/2008 | Korfhage et al. |
| 2008/0227118 A1 | 9/2008 | Kohno et al. |
| 2008/0268514 A1 | 10/2008 | Muller et al. |
| 2008/0307117 A1 | 12/2008 | Muller-Cohn et al. |
| 2009/0010858 A1 | 1/2009 | Asano |
| 2009/0226545 A1 | 9/2009 | Blotsky et al. |
| 2009/0233283 A1 | 9/2009 | Rashtchian et al. |
| 2009/0239208 A1 | 9/2009 | Mayaudon et al. |
| 2009/0259023 A1 | 10/2009 | Su et al. |
| 2009/0291427 A1 | 11/2009 | Muller-Cohn et al. |
| 2009/0298132 A1 | 12/2009 | Muller-Cohn et al. |
| 2009/0312285 A1 | 12/2009 | Fischer et al. |
| 2010/0099150 A1 | 4/2010 | Fang et al. |
| 2010/0159528 A1 | 6/2010 | Liu et al. |
| 2010/0159529 A1 | 6/2010 | Metzler et al. |
| 2010/0178210 A1 | 7/2010 | Hogan et al. |
| 2010/0184069 A1 | 7/2010 | Fernando et al. |
| 2010/0196904 A1 | 8/2010 | Arieli et al. |
| 2010/0209930 A1 | 8/2010 | Fernando |
| 2010/0261252 A1 | 10/2010 | Long et al. |
| 2010/0292447 A1 | 11/2010 | Pitner et al. |
| 2011/0014676 A1 | 1/2011 | Cowan et al. |
| 2011/0027862 A1 | 2/2011 | Bates et al. |
| 2011/0059490 A1 | 3/2011 | Lagunavicius et al. |
| 2011/0081363 A1 | 4/2011 | Whitney et al. |
| 2011/0111410 A1 | 5/2011 | Ryan et al. |
| 2011/0313383 A1 | 12/2011 | Hofstetter et al. |
| 2012/0028933 A1 | 2/2012 | Baust et al. |
| 2012/0052572 A1 | 3/2012 | Whitney et al. |
| 2012/0100522 A1 | 4/2012 | Saghbini et al. |
| 2012/0142070 A1 | 6/2012 | Battrell et al. |
| 2012/0149004 A1 | 6/2012 | Gelfand et al. |
| 2012/0282634 A1 | 11/2012 | Hughes et al. |
| 2012/0295328 A1 | 11/2012 | Wyrich et al. |
| 2013/0066234 A1 | 3/2013 | Helftenbein |
| 2013/0183237 A1 | 7/2013 | Kazimirova et al. |
| 2013/0209997 A1 | 8/2013 | Whitney et al. |
| 2013/0289265 A1 | 10/2013 | Li et al. |
| 2014/0017712 A1 | 1/2014 | Shoji et al. |
| 2014/0065627 A1 | 3/2014 | Whitney et al. |
| 2014/0141411 A1 | 5/2014 | Lloyd, Jr. et al. |
| 2014/0147856 A1* | 5/2014 | Forsyth ............. G01N 33/6896 435/6.15 |
| 2014/0261474 A1 | 9/2014 | Gonda |
| 2015/0329849 A1 | 11/2015 | Whitney et al. |
| 2016/0135446 A1 | 5/2016 | Judy et al. |
| 2016/0338342 A1 | 11/2016 | Whitney et al. |
| 2017/0196220 A1 | 7/2017 | Muller et al. |

(56) References Cited

U.S. PATENT DOCUMENTS

| | | |
|---|---|---|
| 2017/0198335 A1 | 7/2017 | Muller |
| 2017/0202211 A1 | 7/2017 | Muller |

FOREIGN PATENT DOCUMENTS

| | | |
|---|---|---|
| CN | 102026619 A | 4/2011 |
| CN | 102947082 A | 2/2013 |
| CN | 105491883 A | 4/2016 |
| DE | 2424426 A1 | 3/1975 |
| DE | 19834816 A1 | 2/2000 |
| DE | 102008029734 A1 | 12/2009 |
| EP | 0448146 A1 | 9/1991 |
| EP | 0451924 A2 | 10/1991 |
| EP | 0329822 B1 | 6/1994 |
| EP | 0637750 A2 | 2/1995 |
| EP | 0706825 A1 | 4/1996 |
| EP | 0236069 B1 | 5/1997 |
| EP | 0774464 A2 | 5/1997 |
| EP | 0875292 A1 | 11/1998 |
| EP | 0915167 A1 | 5/1999 |
| EP | 1088060 A1 | 4/2001 |
| EP | 0833611 B1 | 8/2001 |
| EP | 0684315 B1 | 6/2002 |
| EP | 0822861 B1 | 11/2003 |
| EP | 1555033 A2 | 7/2005 |
| EP | 1082006 B1 | 2/2006 |
| EP | 0395736 B2 | 8/2006 |
| EP | 1736542 | 12/2006 |
| EP | 1758932 A2 | 3/2007 |
| EP | 1651712 B1 | 10/2007 |
| EP | 2934572 A2 | 10/2015 |
| EP | 3007556 A2 | 4/2016 |
| EP | 3154338 A1 | 4/2017 |
| EP | 3155091 A1 | 4/2017 |
| EP | 3155395 A1 | 4/2017 |
| EP | 3249054 A1 | 11/2017 |
| GB | 2129551 A | 5/1984 |
| JP | S5847492 A | 3/1983 |
| JP | S62502633 A | 10/1987 |
| JP | H08211065 A | 8/1996 |
| JP | H09127106 A | 5/1997 |
| JP | 2000500327 A | 1/2000 |
| JP | 2001050872 A | 2/2001 |
| JP | 2001247401 A | 9/2001 |
| JP | 2009517086 A | 4/2009 |
| JP | 2009096766 A | 5/2009 |
| WO | WO-8607462 A1 | 12/1986 |
| WO | WO-8700196 A1 | 1/1987 |
| WO | WO-8701206 A1 | 2/1987 |
| WO | WO-8900012 A1 | 1/1989 |
| WO | WO-8906542 A1 | 7/1989 |
| WO | WO-9005182 A1 | 5/1990 |
| WO | WO-9114773 A2 | 10/1991 |
| WO | WO-9200091 A1 | 1/1992 |
| WO | WO-9206188 A2 | 4/1992 |
| WO | WO-9206200 A1 | 4/1992 |
| WO | WO-908349 | 5/1992 |
| WO | WO-9209300 A1 | 6/1992 |
| WO | WO-9211864 A1 | 7/1992 |
| WO | WO-9206188 A3 | 10/1992 |
| WO | WO-9422885 A1 | 10/1994 |
| WO | WO-9501559 A2 | 1/1995 |
| WO | WO-9502046 A1 | 1/1995 |
| WO | WO-9510605 A1 | 4/1995 |
| WO | WO-9516198 A1 | 6/1995 |
| WO | WO-9610640 A1 | 4/1996 |
| WO | WO-9636436 A1 | 11/1996 |
| WO | WO-9700670 A1 | 1/1997 |
| WO | WO-9705248 A2 | 2/1997 |
| WO | WO-9715394 A1 | 5/1997 |
| WO | WO-9815355 A2 | 4/1998 |
| WO | WO-9824543 A1 | 6/1998 |
| WO | WO-9955346 A1 | 11/1999 |
| WO | WO-9960849 A1 | 12/1999 |
| WO | WO-9967371 A1 | 12/1999 |
| WO | WO-0009746 A1 | 2/2000 |
| WO | WO-0014505 A1 | 3/2000 |
| WO | WO-0020117 A2 | 4/2000 |
| WO | WO-0062023 A1 | 10/2000 |
| WO | WO-0076664 A1 | 12/2000 |
| WO | WO-0137656 A2 | 5/2001 |
| WO | WO-0194016 A1 | 12/2001 |
| WO | WO-03020874 A2 | 3/2003 |
| WO | WO-03020924 A2 | 3/2003 |
| WO | WO-03056293 A2 | 7/2003 |
| WO | WO-03069344 A1 | 8/2003 |
| WO | WO-03087335 A2 | 10/2003 |
| WO | WO-2004031363 A2 | 4/2004 |
| WO | WO-2004112476 A1 | 12/2004 |
| WO | WO-2005014704 A1 | 2/2005 |
| WO | WO-2005059178 A1 | 6/2005 |
| WO | WO-2005113147 A2 | 12/2005 |
| WO | WO-2005116081 A2 | 12/2005 |
| WO | WO-2006001499 A2 | 1/2006 |
| WO | WO-2007075253 A2 | 7/2007 |
| WO | WO-2007094581 A1 | 8/2007 |
| WO | WO-2008007463 A1 | 1/2008 |
| WO | WO-2008040126 A1 | 4/2008 |
| WO | WO-2008048228 A2 | 4/2008 |
| WO | WO-2008108549 A1 | 9/2008 |
| WO | WO-2009002568 A2 | 12/2008 |
| WO | WO-2009009210 A2 | 1/2009 |
| WO | WO-2009038853 A2 | 3/2009 |
| WO | WO-2010046949 A1 | 4/2010 |
| WO | WO-2010047592 A2 | 4/2010 |
| WO | WO-2010065924 A1 | 6/2010 |
| WO | WO-2010132508 A2 | 11/2010 |
| WO | WO-2010138522 A2 | 12/2010 |
| WO | WO-2012018638 A2 | 2/2012 |
| WO | WO-2012018639 A2 | 2/2012 |
| WO | WO-2012067240 A1 | 5/2012 |
| WO | WO-2012075407 A2 | 6/2012 |
| WO | WO-2012170907 A2 | 12/2012 |
| WO | WO-2013077290 A1 | 5/2013 |
| WO | WO-2014049022 A1 | 4/2014 |
| WO | WO-2014100755 A2 | 6/2014 |
| WO | WO-2015002729 A2 | 1/2015 |
| WO | WO-2015175672 A1 | 11/2015 |
| WO | WO-2015191632 A1 | 12/2015 |
| WO | WO-2015191633 A1 | 12/2015 |
| WO | WO-2015191634 A1 | 12/2015 |
| WO | WO-2017100212 A1 | 6/2017 |
| WO | WO-2017100213 A1 | 6/2017 |
| WO | WO-2018081161 A1 | 5/2018 |

OTHER PUBLICATIONS

"Antibiotics from Prokaryotes." https://www.boundless.com/microbiology/antimicrobial-drugs/commonly-used-antimicrobial-drugs/antibiotics-from-prokaryotes/, downloaded Aug. 1, 2014, 1 page.

Arakawa et al., "Small molecule pharmacological chaperones: From thermodynamic stabilization to pharmaceutical drugs," Biochimica et Biophysica Acta 1764:1677-1687, 2006.

"Are supplements with amino acid chelated minerals better than those with other forms of minerals?" https://www.consumerlab.com/answers/Are+supplements+with+amino+acid+chelated+minerals+better+than+those+with+other+forms+of+minerals%3F/amino_acid_mineral_chelates/, downloaded Jul. 31, 2014, 1 page.

Asano, "Glycosidase inhibitors: update and perspectives on practical use," Glycobiology 13(10):93R-104R, 2003.

Balevicius et al., NMR and quantum chemistry study of mesoscopic effects in ionic liquids. J.Phys.Chem., 114:5365-5371, 2010.

Barnes, The fidelity of Taq polymerase catalyzing PCR is improved by an N-terminal deletion. Gene, 112:29-35 (1992).

Baskakov et al., "Forcing Thermodynamically Unfolded Proteins to Fold," The Journal of Biological Chemistry, 273(9):4831-4834, 1998.

"Borax: Friend or foe?" Momsaware.org webpage, http://www.momsaware.org/household-general/139-borax-friend-or-foe.html, downloaded Jul. 31, 2014, 1 page.

(56) References Cited

OTHER PUBLICATIONS

Boyd et al., "Stabilization Effect of Polyvinyl Alcohol on Horseradish Peroxidase, Glucose Oxidase, 13-Galactosidase and Alkaline Phosphatase," Biotechnology Techniques 10(9):693-698, 1996.
Braasch et al. Locked nucleic acid (LNA): fine-tuning the recognition of DNA and RNA. Chem Bio 8:1-7 (2001).
Branco et al., Preparation and characterization of new room temperature ionic liquids. Chem.Eur.J. 8(16):3671-3677, 2002.
Buhler et al., "Viral Evolution in Response to the Broad-Based Retroviral Protease Inhibitor TL-3," Journal of Virology 75(19):9502-9508, 2001.
Calfon et al. IRE1 couples endoplasmic reticulum load to secretory capacity by processing the XBP-1 mRNA. Nature 415:92-96 (2002) (Abstract only).
Carninci et al., "Thermostabilization and thermoactivation of thermolabile enzymes by trehalose and its application for the synthesis of full length cDNA," Proc. Natl. Acad. Sci. USA 95:520-524, 1998.
Carpenter et al., "Stabilization of phosphofructokinase during air-drying with sugars and sugar/transition metal mixtures," Cryobiology 24(5):455-464, 1987. (Abstract).
Catalan et al., "Progress towards a generalized solvent polarity scale: The solvatochromism of 2-(dimethylamino)-7-nitrofluorene and its homomorph 2-fluoro-7-nitrofluorene", Liebigs Ann. 1995(2):241-252, 1995.
Catalan, Solvent effects based on pure solvent scales. In: Handbook of Solvents. Wypych G., ed. Toronto: ChemTec Publishing and New York: William Andrew Publishing. 2001: 583-616.
Cavalieri et al., "Chaperone-like activity of nanoparticles of hydrophobized poly(vinyl alcohol)," Soft Matter 3:718-724, 2007.
Chen et al., "Stabilization of Recombinant Human Keratinocyte Growth Factor by Osmolytes andSalts," Journal of Pharmaceutical Sciences, 85(4):419-426, 1996.
Cheng et al., "Chip PCR. II. Investigation of different PCR amplification systems in microfabricated silicon-glass chips," Nucleic Acids Res. 24:380-385, 1996.
Chung et al., Lack of Dramatic Enrichment of Fetal DNA in Maternal Plasma by Formaldehyde Treatment, Clinical Chemistry 51(3):655-658 (2005).
Clement et al. Bioactive isomalabaricane triterpenoids from Rhabdastrella globostellata that stabile the binding of DNA polymerase beta to DNA. J. Nat. Prod., 2006, 69(3):373-6.
Clement et al., Following nature's lead: Generating compounds for stabilizing biomolecules. Biopreservation and Biobanking, 2012, 10(4):395-402.
Cohen et al., "Diffusion NMR Spectroscopy in Supramolecular and Combinatorial Chemistry: An Old Parameter—New Insights," Angew. Chem. Int. Ed., 44:520-554, 2005.
Dagani, "Stir, Heat—But No Need to Dissolve," Chemical & Engineering News 81(5): 3 pages, 2003.
Dankwardt et al., "Stabilization of enzyme immunoassays for atrazine," Analytica Chimica Acta 362:35-45, 1998.
Daugherty et al., "Formulation and delivery issues for monoclonal antibody therapeutics," Advanced Drug Delivery Reviews 58:686-706, 2006.
De Sanctis et al., "Influence of Glycerol on the Structure and Redox Properties of Horse Heart Cytochrome c. A Circular Dichroism and Electrochemical Study," Journal of Protein Chemistry, 15(7):599-606, 1996.
Degim et al., "Controlled Delivery of Peptides and Proteins," Current Pharmaceutical Design 13:99-117, 2007.
Del Vigna de Almeida et al., Saliva composition and functions: A comprehensive review. The Journal of Contemporary Dental Practice, 9(3):72-80, 2008.
DePaz et al., "Effects of drying methods and additives on the structure, function, and storage stability of subtilisin: role of protein conformation and molecular mobility," Enzyme and Microbial Technology 31:765-774, 2002.
Di Tullio et al., "Molecular recognition by mass spectrometry," J. Mass Spectrom, 40(7):845-865, 2005.
DNA learning center, "Radiation can cause DNA mutations, 3D animation with narration." http://www.dnalc.org/view/15529-Radiation-can-cause-DNA-mutations-3D-animation-with-narration.html, downloaded Aug. 1, 2014, 1 page.
Dong et al., "Biosynthesis of the Validamycins: Identification of Intermediates in the Biosynthesis of Validamycin A by *Streptomyces hygroscopicus* var. *limoneus*," J. Am. Chem. Soc. 123:2733--2742, 2001.
Dowell et al. Otitis media—principles of judicious use of antimicrobial agents. Pedatrics. 101 Suppl. 1: 165-171, 1998.
Dowell et al. Principles of judicious use of antimicrobial agents for pediatric upper respiratory tract infections. Pedatrics. 101 Suppl. 1: 163-165, 1998.
Dyke et al., "Solvent-Free Functionalization of Carbon Nanotubes," J. Am. Chem. Soc. 125:1156-1157, 2003.
El-Bashiti, "Trehalose Metabolism in Wheat and Identification of Trehalose Metabolizing Enzymes Under Abiotic Stress Conditions," Thesis, The Graduate School of Natural and Applied Sciences of the Middle East Technical University, Jul. 2003, 140 pages.
Ellison et al., Buffer capacities of human blood and plasma. Clinical Chemistry, 4(6):452-461, 1958.
Elzie et al., "The N-terminus of thrombospondin: the domain stands apart," The International Journal of Biochemistry & Cell Biology 36:1090-1101, 2004.
EP11815081.2 Extended European Search Report dated Nov. 5, 2013.
European Patent Application No. 08826300.9 Supplementary Search Report dated Oct. 26, 2010.
European Patent Application No. 10775442.6 Extended European Search Report dated Jan. 21, 2014.
European Patent Application No. 11815082.0 Extended European Search Report dated Nov. 5, 2013.
European Patent Application No. 13865767.1 extended European Search Report dated Oct. 24, 2016.
European Patent Application No. 14819510.0 extended European Search Report dated Feb. 7, 2017.
European Patent Application No. 14819510.0 partial supplementary European Search Report dated Nov. 4, 2016.
European Patent Application No. 15805897.4 extended European Search Report dated Oct. 17, 2017 .
European Patent Application No. 17172030.3 extended European Search Report dated Oct. 13, 2017.
Flaman et al., A rapid PCR fidelity assay. Nucleic Acids Research, 22(15): 3259-3260 (1994).
"Foods high in glycolic acid." http://www.ehow.com/list_5815634_foods-high-glycolic-acid.html , downloaded Jul. 31, 2014, 1 page.
Frye et al., "The kinetic basis for the stabilization of *staphylococcal* nuclease by xylose," Protein Science, 6:789-793, 1997.
Galinski et al., "1,4,5,6-Tetrahydro-2-methyl-4-pyrimidinecarboxylic acid. A novel cyclic amino acid from halophilic phototrophic bacteria of the genus *Ectothiorhodospira*," Eur. J. Biochem., 149:135-139, 1985.
Garcia de Castro et al., "Anhydrobiotic Engineering of Gram-Negative Bacteria," Applied and Environmental Microbiology 66(9):4142-4144, 2000.
Gerard et al., cDNA synthesis by moloney murine leukemia virus RNase H-minus reverse transcriptase possessing full DNA polymerase activity. Focus, 14(1): 91-93 (1992).
Godfrey, "Solvent selection via miscibility number," Chem. Technol. 2(6):359-363, 1972.
Goller et al, Protection of a model enzyme (lactate dehydrogenase) against heat, urea and freeze-thaw treatment by compatible solute additives, J. of Molecular Catalsys B: Enzymatic, 7(104):37-45,1999.
Gombotz et al., "Biodegradable Polymers for Protein and Peptide Drug Delivery," Bioconjugate Chem. 6:332-351, 1995.
Gowrishankar et al., Osmoregulation in Enterobacteriaceae: Role of proline/Betaine transport systems. Current Science, 57(5): 225-234 (1988).
Green DR, "Apoptosis. Death deceiver," Nature, 396(6712):629-630, 1998.
Green DR, "Apoptotic pathways: the roads to ruin," Cell, 94(6):695-69, 1998.

(56) References Cited

OTHER PUBLICATIONS

Green et al., "Mitochondria and apoptosis," Science, 281(5381):1309-1312, 1998.
Harding et al., Perk Is Essential for Translational Regulation and Cell Survival during the Unfolded Protein Response. (2000) Mol Cell 5:897-904. doi: 10.1016/s1097-2765(00)80330-5.
Hatam & Kayden, A High-Performance Liquid Chromatographic Method for the Determination of Tocopherol in Plasma and Cellular Elements of the Blood, Journal of Lipid Research 20:639-645 (1979).
Haze et al., Mammalian Transcription Factor ATF6 Is Synthesized as a Transmembrane Protein and Activated by Proteolysis in Response to Endoplasmic Reticulum Stress. (1999) Mol Biol Cell 10(11):3787-3799. doi: 10.1091/mbc.10.11.3787.
Henke et al., Betaine improves the PCR amplification of GC-rich DNA sequences. Nucleic Acids Research, 25(19): 3957-3958 (1997).
Hewetson et al., Sucrose concentration in blood: A new method for assessment of gastric permeability in horses with gastric ulceration. J.Vet.Inter.Med., 20:388-394, 2006.
Hoffman, "Hydrogels for biomedical applications," Advanced Drug Delivery Reviews 43:3-12, 2002.
Holland et al., "Biological sample collection and processing for molecular epidemiological studies," Mutation Research 543:217-234, 2003.
Holland et al., "Molecular epidemiology biomarkers—Sample collection and processing considerations," Toxicology and Applied Pharmacology 206:261-268, 2005.
Houts et al., Reverse transcriptase from avian myeloblastosis virus. Journal of Virology, 29(2): 517-522 (1979).
Iyer et al, Enzyme stability and stabilization—Aqueous and non-aqueous environment, Process Biochemistry, 43:1019-1032 (2008).
Jin et al., Effect of mobile phase additives on resolution of some nucleic compounds in high performance liquid chromatography. Biotechnology and Bioprocess Engineering, 12:525-530, 2007.
Jones et al., "Long-term storage of DNA-free RNA for use in vaccine studies," BioTechniques 43(5):675-681, 2007.
Kaijalainen et al., "An alternative hot start technique for PCR in small volumes using beads of wax-embedded reaction components dried in trehalose," Nucleic Acids Research 21(12):2959-2960, 1993.
Kameda et al., "New Cyclitols, Degradation of Validamycin A by Flavobacterium Saccharophilum," The Journal of Antibiotics 33(12):1573-1574, 1980.
Kaufman. Orchestrating the unfolded protein response in health and disease. J Clin Invest 110(10):389-1398 (2002).
Kilger and Paabo, Direct DNA sequence determination from total genomic DNA. Nucleic Acids Research, 25(10): 2032-2034 (1997).
Kim et al., Chemical Biology Investigation of Cell Death Pathways Activated by Endoplasmic Reticulum Stress Reveals Cytoprotective Modulators of ASK1. J. Biol. Chem. 284(3):1593-1603 (2009).
Kirn-Safran et al., "Heparan Sulfate Proteoglycans: Coordinators of Multiple Signaling Pathways during Chondrogenesis," Birth Defects Research (Part C) 72:69-88, 2004.
Knapp et al., "Extrinsic protein stabilization by the naturally occurring osmolytes β-hydroxyectoine and betaine," Extremophiles, 3:191-198, 1999.
Knuesel et al., "Comparative studies of suidatrestin, a specific inhibitor of trehalases," Comparative Biochemistry and Physiology Part B 120:639-646, 1998.
Komiyama et al., "Hydrolysis of DNA and RNA by lanthanide ions: mechanistic studies leading to new applications," Chem. Commun.:1443-1451, 1999.
Konishi et al., "Effects of Bay m 1099, an a-Glucosidase Inhibitor, on Starch Degradation in Germinating Mung Beans," Biosci. Biotechnol. Biochem. 62(1):142-144, 1998.
Kotewicz et al., Isolation of closed Moloney murine leukemia virus reverse transcriptase lacking ribonuclease H activity. Nucleic Acid Research, 16(1): 265 (1988).
Kravitz, Lactate: Not guilty as charged. IDEA Fitness Journal 2(6), 23-25 (2005) http://www.unm.edu/lkravitz/Article%20folder/lactate.html, 3d paragraph, downloaded Jul. 31, 2014.
Kricka and Wilding, "Microchip PCR," Anal. Bioanal. Chem 377:820-825 (2003).
Kudo et al., A molecular chaperone inducer protects neurons from ER stress. Cell Death and Differentiation, 15:364-375 (2008).
Kumar et al., "The role of proline in the prevention of aggregation during protein folding in vitro," Biochemistry and Molecular Biology International, 46(3):509-517, 1998.
Langer. New methods of drug delivery. Science, New Series, vol. 249, No. 4976 (Sep. 28, 1990), pp. 1527-1533.
Langer, "Polymer-Controlled Drug Delivery Systems," Acc. Chem. Res. 26:537-542, 1993.
Lawyer et al., High-level expression, purification, and enzymatic characterization of full-length Thermus aquaticus DNA polymerase and a truncated form deficient in 5' to 3' exonuclease activity. PCR Methods and Applications, Cold Spring Harbor Laboratory Press, 2:275-287 (1993).
Lee et al., "Analysis of the S3 and S3' subsite specificities of feline immunodeficiency virus (FIV) protease: Development of a broad-based protease inhibitor efficacious against FIV, SW, and HIV in vitro and ex vivo," Proc. Natl. Acad. Sci. USA 95:939-944, 1998.
Lee et al., "Development of a New Type of Protease Inhibitors, Efficacious against FIV and HIV Variants," J. Am. Chem. Soc. 121:1145-1155, 1999.
L-glutamine Product catalog. GlutaMAX media. Keep your cells healthier longer. Thermo Fisher Scientific Inc., 2015. Retrieved from the internet on Feb. 16, 2018, 3 pages.
Li et al., "Effect of Mobile Phase Additives on the Resolution of Four Bioactive Compounds by RP-HPLC", Int'l Journal of Molecular Sciences, 11(5):2229-2240 (Jan. 2010).
Liao et al., "The effects of polyvinyl alcohol on the in vitro stability and delivery of spray-dried protein particles from surfactant-free HFA 134a-based pressurised metered dose inhalers," International Journal of Pharmaceutics 304:29-39, 2005.
Loo et al., Peptide and Protein Analysis by Electrospray Ionization—MassSpectrometry and Capillary Electrophoresis-Mass Spectrometry, Anal. Biochem., 179(2):404-412 (1989).
Lou et al., "Increased amplification efficiency of microchip-based PCR by dynamic surface passivation," Biotechniques, vol. 36, No. 2, pp. 248-252 (2004).
Lozano et al., Stabilization of x-Chymotrypsin by iconic liquids in transesterification reactions. Biotechnology and Bioengineerig, 75(5):563-569 (2001).
Luo et al., "Expression of a fusion protein of scFv-biotin mimetic peptide for immunoassay," J. Biotechnol. 65:225, 1998.
Malin et al., "Effect of Tetrahydropyrimidine Derivatives on Protein-Nucleic Acids Interaction," The Journal of Biological Chemistry, 274(11):6920-6929, 1999.
Manzanera et al., "Hydroxyectoine Is Superior to Trehalose for Anhydrobiotic Engineering of Pseudomanas putida KT2440," Applied and Environmental Microbiology 68(9):4328-4333, 2002.
Manzanera et al., "Plastic Encapsulation of Stabilized *Escherichia coli* and Pseudomonas putida," Applied and Environmental Microbiology 70(5):3143-3145, 2004.
Marshall et al.,"NXY-059, a Free Radical-Trapping Agent, Substantially Lessens the Functional Disability Resulting From Cerebral Ischemia in a Primate Species," Stroke, 32:190-198, 2001.
Mascellani et al., "Compatible solutes from hyperthermophiles improve the quality of DNA microarrays," BMC Biotechnology, 7(82):1-6, 2007.
Mitchell et al., "Dispersion of Functionalized Carbon Nanotubes in Polystyrene," Macromolecules 35:8825-8830, 2002.
Mizuguchi et al., Characterization and application to hot start PCR of neutralizing momoclonal antibodies against KOD DNA polymerase J.Biochem., 126:762-768 (1999).
Mohr, "Reversible chemical reactions as the basis for optical sensors used to detect amines, alcohols and humidity," J. Mater. Chem., 9:2259-2264, 1999.
Mori K, Tripartite Management Mini review of Unfolded Proteins in the Endoplasmic Reticulum. Cell 101(5):451-454 (2000).

(56) References Cited

OTHER PUBLICATIONS

Natale et al., Sensitivity of Bovine Blastocyst Gene Expression Patterns to Culture Environments Assessed by Differential Display RT-PCR. Reproduction, 122 (5): 687-693, 2001.
New England Biolabs 1993/1994, 4 pages.
Nielsen et al., Peptide nucleic acid (PNA). A DNA mimic with a peptide backbone. Bioconjugate Chemistry, 5:3-7 (1994).
O'Brien et al. Acute sinusitis–principles of judicious use of antimicrobial agents. Pediatrics. 101 Suppl. 1: 174-177, 1998.
O'Brien et al. Cough illness/bronchitis—principles of judicious use of antimicrobial agents. Pediatrics. 101 Suppl. 1: 178-181, 1998.
Okada et al. Distinct roles of activating transcription factor 6 (ATF6) and double-stranded RNA-activated protein kinase-like endoplasmic reticulum kinase (PERK) in transcription during the mammalian unfolded protein response. Biochem J 366(Pt 2):585-594 (2002).
Ortega et al., "New functional roles for non-collagenous domains of basement membrane collagens," Journal of Cell Science 115:4201-4214, 2002.
Parsegian et al., "Macromolecules and Water: Probing with Osmotic Stress," Methods in Enzymology, 259:43-94, 1995.
Pasloske et al., Armored RNA technology for production of ribonuclease-resistant viral RNA controls and standards. J Clin Microbiol. ;36(12):3590-3594 (1998).
Passot et al., "Physical characterization of formulations for the development of two stable freeze-dried proteins during both dried and liquid storage," European Journal of Pharmaceutics and Biopharmaceutics 60:335-348, 2005.
Pavlov et al., "The Role of ECM Molecules in Activity-Dependent Synaptic Development and Plasticity," Birth Defects Research (Part C) 72:12-24, 2004.
PCT Patent Application No. PCT/US2013/077290 International Preliminary Report on Patentability dated Jul. 2, 2015.
PCT Patent Application No. PCT/US2013/077290 International Search Report and Written Opinion dated Jun. 23, 2014.
PCT Patent Application No. PCT/US2014/042396 International Search Report dated Mar. 13, 2015.
PCT Patent Application No. PCT/US2014/042396 International Preliminart Report on Patentability dated Dec. 23, 2015.
PCT Patent Application No. PCT/US2014/042396 Written Opinion dated Mar. 13, 2015.
PCT Patent Application No. PCT/US2015/034967 International Search Report and Written Opinion dated Sep. 8, 2015.
PCT Patent Application No. PCT/US2015/034968 International Search Report and Written Opinion dated Sep. 16, 2015.
PCT Patent Application No. PCT/US2015/034969 International Preliminary Report on Patentability dated Dec. 22, 2016.
PCT Patent Application No. PCT/US2015/034969 International Search Report and Written Opinion dated Sep. 15, 2015.
PCT Patent Application No. PCT/US2016/065200 International Search Report and Written Opinion dated Feb. 16, 2017.
PCT Patent Appliction No. PCT/US2016/065198 International Search Report and Written Opinion dated Mar. 13, 2017.
PCT/US2005/012084 International Preliminary Report on Patentability dated Oct. 11, 2006.
PCT/US2005/012084 International Search Report dated Feb. 7, 2006.
PCT/US2006/45661 International Preliminary Report on Patentability dated Jun. 30, 2008.
PCT/US2006/45661 International Search Report and Written Opinion dated Nov. 13, 2007.
PCT/US2008/061332 International Preliminary Report on Patentability dated Oct. 27, 2009.
PCT/US2008/061332 International Search Report and Written Opinion dated Jul. 29, 2009.
PCT/US2008/068628 International Preliminary Report on Patentability dated Jan. 5, 2010.
PCT/US2008/068628 International Search Report and Written Opinion dated Aug. 27, 2009.
PCT/US2010/34454 International Preliminary Report on Patentability dated Nov. 15, 2011.
PCT/US2010/34454 International Search Report and Written Opinion dated Jan. 20, 2011.
PCT/US2011/045404 International Preliminary Report on Patentability dated Jan. 29, 2013.
PCT/US2011/045404 International Search Report and Written Opinion dated Mar. 27, 2012.
PCT/US2011/045405 International Preliminary Report on Patentability dated Jan. 29, 2013.
PCT/US2011/045405 International Search Report and Written Opinion dated Mar. 26, 2012.
PCT/US2016/065198 International Preliminary Report on Patentability dated Jun. 12, 2018.
PCTUS2016/065200 International Preliminary Report on Patentability dated Jun. 12, 2018.
PCT/US2017/058136 International Search Report and Written Opinion dated Dec. 21, 2017.
Peters et al., Sensitivity of human, murine, and rat cells to 5-Fluorouracil and 5'-Deoxy-5-fluorounidine in relation to drug-metabolozing enzymes Cancer Research, 46:20-28 (1986).
Pickering, LK, Ed. Red Book: Report of the Committee on Infectious Diseases, 26th edition. Elk Grove Village, IL, pp. 695-697, 2003.
"Polyvinyl alcohol." Wikipedia, 6 pages, printed Oct. 17, 2017 from: https://en.wikipedia.org/wiki/Polyvinyl_alcohol.
Prestrelski et al., "Dehydration induced Conformational Transitions in Proteins and Their Inhibition by Stabilizers," Biophysical Journal 65:661-671, 1993.
Qu et al., Ambient stable quantitative PCR reagents for the detection of Yersinia pestis. PLoS Neglected Tropical Diseases, Mar. 2010, 4(3):e629.
Roberts, "Organic compatible solutes of halotolerant and halophilic microorganisms," Saline Systems, 1(5):1-30, 2005.
Roche. "PCR Reaction Components." Downloaded from the internet (http://www.roche-appliedscience.com/sis/amplification/per_amplification_050300.html; Downloaded on Dec. 13, 2012, 4 pages.
Ron et al. Signal integration in the endoplasmic reticulum unfolded protein response. Nat Rev Mol Cell Biol 8:519-529 (2007).
Rosenstein et al. The common cold—principles of judicious use of antimicrobial agents. Pediatrics. 101 Suppl. 1: 181-184, 1998.
Sadeghi et al., Effect of alkyl chain length and temperature on the thermodynamic properties of ionic liquids 1-alkyl-3-methylimidazolium bromide in aqueous and non-aqueous solutions at different temperatures. J.Chem.Thermodynamics, 41:273-289, 2009.
Saiki et al. Primer-Directed Enzymatic Amplification of DNA with a Thermostable DNA Polymerase. Science 239:487-491 (1988).
Sauer et al., "Bacterial Milking: A Novel Bioprocess for Production of Compatible Solutes,"Biotechnology and Bioengineering, 57(3):306-313, 1998.
Sawicki, "Foods high in Glutathione." http://www.ehow.com/list_6900955_foods-high-glutathione.html, downloaded Jul. 31, 2014, 1 page.
Schnoor, et al. Characterization of the synthetic compatible solute homoectoine as a potent PCR enhancer. Biochem and Biophys. Res. Comm, 2004, 322:867-872.
Schwartz et al. Pharyngitis—principles of judicious use of antimicrobial agents. Pediatrics. 101 Suppl. 1: 171-174, 1998.
Schyma, "Erfahrungen mit der PVAL-Methode in der rechtsmedizinischen Praxis," Arch. Kriminol. 97(1-2):41-46, 1996.
Schyma et al., "DNA-PCR Analysis of Bloodstains Samples by the Polyvinyl-Alcohol Method," Journal of Forensic Sciences 44(1):95-99, 1999.
Schyma et al., "The Accelerated Polyvinyl-Alcohol Method for GSR Collection-PVAL 2.0," Journal of Forensic Sciences 45(6):1303-1306, 2000.
Scouten, "A survey of enzyme coupling techniques," Methods in Enzymology, 135:30-65, 1987.
Sigma Catalog. St. Louis:Sigma-Aldrich. p. 1987 (1998).
Sirieix-Plenet et al., "Behaviour of a binary solvent mixture constituted by an amphiphilic ionic liquid, 1-decyl-3-methylimidazolium bromide and water Potentiometric and conductimetric studies," Talanta 63(4):979-986, Jul. 8, 2004.

(56) References Cited

OTHER PUBLICATIONS

Slita et al., "DNA-polycation complexes Effect of polycation structure on physico-chemical and biological properties," Journal of Biotechnology, 127:679-693, 2007.
Smith et al., "Optimal Storage Conditions for Highly Dilute DNA Sampled: A Role for Trehalose as a Preserving Agent," Journal of Forensic Science 50(5):1-8, 2005.
Sola-Penna et al., "Carbohydrate protection of enzyme structure and function against guanidinium chloride treatment depends on the nature of carbohydrate and enzyme," Eur. J. Biochem., 248:24-29, 1997.
Soltis and Skalka, The alpha and beta chains of avian retrovirus reverse transcriptase independently expressed in *Escherichia coli*: Characterization of enzymatic activities. Proc. Nat. Acad. Sci. USA, 85:3372-3376 (1968).
Spiess et al., Trehalose is a potent PCR enhancer: Lowering of DNA melting temperature and thermal stabilization of Taq polymerase by the disaccharide trehalose. Clinical Chemistry, 2004, 50:1256-1259.
Srinivasan et al., Review—Effect of Fixatives and Tissue Processing on the Content and Integrity of Nucleic Acids, American Journal of Pathology 161(6): 1961-1971 (Dec. 2002).
Stein and Moore, The free amino acids of human blood plasma. JCB, 211:915-926, 1954.
Stock et al., Effects of ionic liquids on the acetylcholinesterase—A structure-activity relationship consideration. Green Chemistry, 6:286-290, 2004.
Suslick et al., "Colorimetric sensor arrays for molecular recognition," Tetrahedron 60:11133-11138, 2004.
Tanriverdi et al., A rapid and automated sample-to-result HIV load test for near-patient application. Journal of Infectious Diseases, 201(S1):S52-S58, 2010.
"The dose makes the poison." Yale chemsafe (http://learn.caim.yale.edu/chemsafe/references/dose.html, downloaded Aug. 1, 2014, 1 page.
The Frontier energy solution, Inc.'s FAQ, http://www.frontierenergysolutionsinc.com/faq/, downloaded Jul. 31, 2014.
Timasheff, "Water as Ligand: Preferential Binding and Exclusion of Denaturants in Protein Unfolding," Biochemistry, 31(41):9857-9864, 1992.
U.S. Appl. No. 11/291,267 Office action dated Jun. 13, 2014.
U.S. Appl. No. 12/182,926 Office action dated Apr. 30, 2014.
U.S. Appl. No. 13/191,346 Office action dated Jul. 22, 2014.
U.S. Appl. No. 11/102,588 Notice of Allowance dated Sep. 24, 2014.
U.S. Appl. No. 11/291,267 Office Action dated Mar. 12, 2015.
U.S. Appl. No. 12/509,303 Final Office action dated Jun. 9, 2014.
U.S. Appl. No. 13/191,346 Office Action dated Mar. 20, 2015.
U.S. Appl. No. 13/812,288 Restriction Requirement dated Oct. 9, 2014.
U.S. Appl. No. 13/966,117 Final Office Action dated Feb. 26, 2015.
U.S. Appl. No. 13/966,117 Office action dated Sep. 25, 2014.
U.S. Appl. No. 13/191,346 Office Action dated Jul. 2, 2015.
U.S. Appl. No. 13/812,288 Office Action dated Aug. 25, 2016.
U.S. Appl. No. 13/812,288 Office Action dated Feb. 1, 2017.
U.S. Appl. No. 13/812,288 Office Action dated Feb. 11, 2016.
U.S. Appl. No. 13/812,288 Office Action dated Jan. 12, 2017.
U.S. Appl. No. 13/812,288 Office Action dated May 7, 2015.
U.S. Appl. No. 14/895,475 Office Action dated Dec. 12, 2017.
U.S. Appl. No. 14/895,475 Office Action dated Jan. 10, 2017.
U.S. Appl. No. 14/895,475 Office Action dated May 22, 2017.
U.S. Appl. No. 15/164,531, filed Oct. 20, 2017.
Vanin, "Iron diethyldithiocarbamate as spin trap for nitric oxide detection," Meth. Enzymol., 301:269-79, 1999.
Voziyan et al., "Chaperonin-assisted folding of glutamine synthetase under nonpermissive conditions: Off-pathway aggregation propensity does not determine the co-chaperonin requirement," Protein Science, 9:2405-2412, 2000.
Wang et al., "A Naturally Occurring Protective System in Urea-Rich Cells: Mechanism of Osmolyte Protection of Proteins against Urea Denaturation," Biochemistry, 36:9101-9108, 1997.
Wang et al., "Antibody Structure, Instability, and Formulation," Journal of Pharmaceutical Sciences 96(1):1-26, 2007.
Wang et al., "Instability, stabilization, and formulation of liquid protein pharmaceuticals," International Journal of Pharmaceutics 185:129-188, 1999.
Wang, "Protein aggregation and its inhibition in biopharmaceutics," International Journal of Pharmaceutics 289:1-30, 2005.
Whitman et al., "Prokaryotes: the unseen majority," Proc. Natl. Acad. Sci. USA, 95:6578-6583, 1998.
Whittlesey et al., "Delivery systems for small molecule drugs, proteins, and DNA: the neuroscience/biomaterial interface," Experimental Neurology 190:1-16, 2004.
Wierzbicka-Patynowski et al., "The ins and outs of fibronectin matrix assembly," Journal of Cell Science 116:3269-3276, 2003.
Yamamoto et al., "Molecular Design of Bioconjugated Cell Adhesion Peptide with a Water-Soluble Polymeric Modifier for Enhancement of Antimetastatic Effect," Current Drug Targets 3:123-130, 2002.
Yancey et al., "Living with Water Stress: Evolution of Osmolyte Systems," Science, 217:1214-1222, 1982.
Yang et al., Neuroprotection by 2-h postischemia administration of two free radical scavengers, alpha-phenyl-n-tert-butyl-nitrone (PBN) and N-tert-butyl-(2-sulfophenyl)-nitrone (S-PBN), in rats subjected to focal embolic cerebral ischemia., Exp. Neurol., 163(1):39-45, 2000.
Yoshida et al. Identification of the cis-Acting Endoplasmic Reticulum Stress Response Element Responsible for Transcriptional Induction of Mammalian Glucose-Regulated Proteins. J Biol Chem 273:33741-33749 (1998).
Zhang et al., Effect of Formaldehyde Treatment on the Recovery of Cell-Free Fetal DNA from Maternal Plasma at Different Processing Times, Clinica Chimica Acta 397:6-64 (2008).
Zhao et al., "NXY-059, a novel free radical trapping compound, reduces cortical infarction after permanent focal cerebral ischemia in the rat," Brain Res., 909(1-2):46-50, 2001.
Zhi et al., "Renaturation of citrate synthase: Influence of denaturant and folding assistants," Protein Science, 1:522-529, 1992.

\* cited by examiner

0h

6h

24h

REDUCTION OF ERYTHROCYTE SEDIMENTATION RATE

CROSS-REFERENCE

This application is a U.S. National Phase Application of International Application No. PCT/US2016/065198, filed on Dec. 6, 2016, and claims the benefit of US U.S. Provisional Application No. 62/264,786, filed Dec. 8, 2015. The disclosure of each of the prior applications is considered part of and is incorporated by reference in the disclosure of this application.

BACKGROUND OF THE INVENTION

There exists a need for improved formulations and methods for reducing the rate of blood sedimentation for a time sufficient for storage, transport, and shipping for research, diagnostic and therapeutic purposes.

The present invention relates generally to the reduction of sedimentation rate of one or more erythrocytes in a blood sample. In particular, the invention relates to formulations, compositions, articles of manufacture, kits and methods for the reduction of erythrocyte sedimentation rate in a blood sample.

SUMMARY OF THE INVENTION

Described herein, in some embodiments, are in vitro methods for reducing the erythrocyte sedimentation rate in a blood sample, comprising: combining a sample of blood with an amount of a formulation comprising sucralose, wherein the amount is sufficient to produce a treated blood sample having a sucralose concentration of at least about 5 mM sucralose, thereby reducing the erythrocyte sedimentation rate as compared to erythrocyte sedimentation rate in an untreated blood sample. In some embodiments, the treated blood sample has a sucralose concentration of about 5 mM sucralose to about 100 mM sucralose. In some embodiments, the treated blood sample has a sucralose concentration of about 10 mM sucralose to about 100 mM sucralose. In some embodiments, the treated blood sample has a sucralose concentration of about 20 mM sucralose to about 100 mM sucralose. In some embodiments, the treated blood sample has a sucralose concentration of about 24 mM sucralose to about 100 mM sucralose. In some embodiments, the treated blood sample has a sucralose concentration of about 15 mM sucralose to about 50 mM sucralose. In some embodiments, the treated blood sample has a sucralose concentration of about 5 mM sucralose to about 50 mM sucralose. In some embodiments, the treated blood sample has a sucralose concentration of about 5 mM sucralose to about 40 mM sucralose. In some embodiments, the treated blood sample has a sucralose concentration of about 10 mM sucralose to about 35 mM sucralose. In some embodiments, the treated blood sample has a sucralose concentration of about 10 mM sucralose to about 30 mM sucralose. In some embodiments, the treated blood sample has a sucralose concentration of about 5 mM sucralose to about 25 mM sucralose. In some embodiments, the treated blood sample has a sucralose concentration of about 5 mM sucralose up to but not including 25 mM sucralose. In some embodiments, the treated blood sample has a sucralose concentration of about 5 mM sucralose to about 20 mM sucralose. In some embodiments, the treated blood sample has a sucralose concentration of about 5 mM sucralose to about 15 mM sucralose. In some embodiments, the treated blood sample has a sucralose concentration of about 5 mM sucralose to about 10 mM sucralose. In some embodiments, the treated blood sample has a sucralose concentration of about 24 mM. In some embodiments, the treated blood sample has a sucralose concentration of about 25 mM. In some embodiments, erythrocyte sedimentation rate is reduced by at least 10%, at least 20%, at least 30%, at least 40%, at least 50%, at least 60%, at least 70%, at least 80%, at least 90%, at least 95% of the erythrocyte sedimentation rate of the untreated blood sample. In some embodiments, the formulation is in the form of a powder, a solid, a lyophilized form, a solution, or an aqueous solution. In some embodiments, the formulation is a powder. In some embodiments, the formulation is a solid. In some embodiments, the formulation is lyophilized. In some embodiments, the formulation is a solution. In some embodiments, the solution is an aqueous solution. In some embodiments, the formulation consists of sucralose. In some embodiments, the formulation further comprises an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid ($K_3$EDTA), di-potassium ethylenediaminetetraacetic acid ($K_2$EDTA), hirudin, and sodium polyanethol sulfonate (SPS). In some embodiments, the anticoagulant is acid citrate dextrose solution (ACD). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid ($K_3$EDTA). In some embodiments, the anticoagulant is di-potassium ethylenediaminetetraacetic acid ($K_2$EDTA). In some embodiments, the anticoagulant is hirudin. In some embodiments, the anticoagulant is sodium polyanethol sulfonate (SPS). In some embodiments, the formulation is contained within a blood collection tube, and the combining step occurs within the blood collection tube. In some embodiments, the blood collection tube is an evacuated blood collection tube. In some embodiments, the blood is collected from a subject. In some embodiments, the subject is a mammal. In some embodiments, the subject is a human.

Described herein, in some embodiments, are in vitro methods for maintaining one or more erythrocytes in suspension in a blood sample, comprising: combining a sample of blood with an amount of a formulation comprising sucralose, wherein the amount is sufficient to produce a treated blood sample having a sucralose concentration of at least about 5 mM sucralose, thereby maintaining the one or more erythrocytes in suspension for a period of at least 30 minutes as compared to an untreated blood sample. In some embodiments, the one or more erythrocytes remain in suspension for a period of at least 10 minutes, at least 20 minutes, at least 30 minutes, at least 40 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 10 hours, at least 12 hours, at least 24 hours or at least 48 hours. In some embodiments, the treated blood sample has a sucralose concentration of about 5 mM sucralose to about 100 mM sucralose. In some embodiments, the treated blood sample has a sucralose concentration of about 10 mM sucralose to about 100 mM sucralose. In some embodiments, the treated blood sample has a sucralose concentration of about 20 mM sucralose to about 100 mM sucralose. In some embodiments, the treated blood sample has a sucralose concentration of about 24 mM sucralose to about 100 mM sucralose. In some embodiments, the treated blood sample has a sucralose concentration of about 15 mM sucralose to about 50 mM sucralose. In some embodiments, the treated blood sample has a sucralose concentration of about 5 mM sucralose to about 50 mM sucralose. In some embodiments, the treated blood sample has a sucralose concentration of about 5 mM sucralose to about 40 mM sucralose. In some embodiments, the treated blood sample has a sucralose concentration of about 10 mM sucralose to about 35 mM sucralose. In some embodiments, the treated blood sample has a sucralose concentration of about 10 mM sucralose to about 30 mM sucralose. In some embodiments, the treated blood sample has a sucralose concentration of about 5 mM sucralose to about 25 mM sucralose. In some embodiments, the treated blood sample has a sucralose concentration of about 5 mM sucralose up to but not including 25 mM sucralose. In some embodiments, the treated blood sample has a sucralose concentration of about 5 mM sucralose to about 20 mM sucralose. In some embodiments, the treated blood sample has a sucralose concentration of about 5 mM sucralose to about 15 mM sucralose. In some embodiments, the treated blood sample has a sucralose concentration of about 5 mM sucralose to about 10 mM sucralose. In some embodiments, the treated blood sample has a sucralose concentration of about 24 mM. In some embodiments, the treated blood sample has a sucralose concentration of about 25 mM. In some embodiments, at least 10%, at least 20%, at least 30%, at least 40%, at least 50%, at least 60%, at least 70%, at least 80%, at least 90%, at least 95% of the one or more erythrocytes remain in suspension in the treated blood sample as compared to the untreated blood sample. In some embodiments, the formulation is a powder. In some embodiments, the formulation is a solid. In some embodiments, the formulation is lyophilized. In some embodiments, the formulation is a solution. In some embodiments, the solution is an aqueous solution. In some embodiments, the formulation consists of sucralose. In some embodiments, the formulation further comprises an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid ($K_3$EDTA), di-potassium ethylenediaminetetraacetic acid ($K_2$EDTA), hirudin, and sodium polyanethol sulfonate (SPS). In some embodiments, the anticoagulant is acid citrate dextrose solution (ACD). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid ($K_3$EDTA). In some embodiments, the anticoagulant is di-potassium ethylenediaminetetraacetic acid ($K_2$EDTA). In some embodiments, the anticoagulant is hirudin. In some embodiments, the anticoagulant is sodium polyanethol sulfonate (SPS). In some embodiments, the formulation is contained within a blood collection tube, and the combining step occurs within the blood collection tube. In some embodiments, the blood collection tube is an evacuated blood collection tube. In some embodiments, the blood sample is collected from a subject. In some embodiments, the subject is a mammal. In some embodiments, the subject is a human.

Described herein, in some embodiments, are compositions comprising a blood sample and sucralose, wherein the sucralose is at a concentration of about 5 mM sucralose up to about 100 mM sucralose. In some embodiments, the sucralose is at a concentration of about 10 mM sucralose to about 100 mM sucralose. In some embodiments, the sucralose is at a concentration of about 20 mM sucralose to about 100 mM sucralose. In some embodiments, the sucralose is at a concentration of about 24 mM sucralose to about 100 mM sucralose. In some embodiments, the sucralose is at a concentration of about 15 mM sucralose to about 50 mM sucralose. In some embodiments, the sucralose is at a concentration of about 5 mM sucralose to about 50 mM sucralose. In some embodiments, the sucralose is at a concentration of about 5 mM sucralose to about 40 mM sucralose. In some embodiments, the treated blood sample has a sucralose concentration of about 10 mM sucralose to about 35 mM sucralose. In some embodiments, the treated blood sample has a sucralose concentration of about 10 mM sucralose to about 30 mM sucralose. In some embodiments, the sucralose is at a concentration of about 5 mM sucralose up to but not including 25 mM sucralose. In some embodiments, the sucralose is at a concentration of about 5 mM sucralose to about 20 mM sucralose. In some embodiments, the sucralose is at a concentration of about 5 mM sucralose to about 15 mM sucralose. In some embodiments, the sucralose is at a concentration of about 5 mM sucralose to about 10 mM sucralose. In some embodiments, the treated blood sample has a sucralose concentration of about 24 mM. In some embodiments, the treated blood sample has a sucralose concentration of about 25 mM. In some embodiments, the compositions further comprise an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid ($K_3$EDTA), di-potassium ethylenediaminetetraacetic acid ($K_2$EDTA), hirudin, and sodium polyanethol sulfonate (SPS). In some embodiments, the anticoagulant is acid citrate dextrose solution (ACD). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid ($K_3$EDTA). In some embodiments, the anticoagulant is di-potassium ethylenediaminetetraacetic acid ($K_2$EDTA). In some embodiments, the anticoagulant is hirudin. In some embodiments, the anticoagulant is sodium polyanethol sulfonate (SPS). In some embodiments, the composition is contained within a blood collection tube. In some embodiments, the blood collection tube is an evacuated blood collection tube. In some embodiments, the blood is collected from a subject. In some embodiments, the subject is a mammal. In some embodiments, the subject is a human.

Described herein, in some embodiments, are articles of manufacture, comprising sucralose contained within a blood collection tube, wherein the sucralose is in a quantity sufficient to produce a final concentration of about 5 mM sucralose to about 100 mM sucralose in the blood sample. In some embodiments, the sucralose is in a quantity sufficient to produce a final concentration of about 10 mM sucralose to about 100 mM sucralose. In some embodiments, the sucralose is in a quantity sufficient to produce a final concentration of about 20 mM sucralose to about 100 mM sucralose. In some embodiments, the sucralose is in a quantity sufficient to produce a final concentration of about 24 mM sucralose to about 100 mM sucralose. In some embodiments, the sucralose is in a quantity sufficient to produce a final concentration of about 15 mM sucralose to about 50 mM sucralose. In some embodiments, the sucralose is in a quantity sufficient to produce a final concentration of about 5 mM sucralose to about 50 mM sucralose in the blood sample. In some embodiments, the sucralose is in a quantity sufficient to produce a final concentration of about 5 mM sucralose to about 40 mM sucralose in the blood sample. In some embodiments, the treated blood sample has a sucralose concentration of about 10 mM sucralose to about 35 mM sucralose. In some embodiments, the treated blood sample has a sucralose concentration of about 10 mM sucralose to about 30 mM sucralose. In some embodiments, the sucralose is in a quantity sufficient to produce a final concentration of about 5 mM sucralose to up to but not including 25 mM sucralose in the blood sample. In some embodiments, the sucralose is in a quantity sufficient to produce a final concentration of about 5 mM sucralose to about 20 mM sucralose in the blood sample. In some embodiments, the sucralose is in a quantity sufficient to produce a final concentration of about 5 mM sucralose to about 15 mM sucralose in the blood sample. In some embodiments, the sucralose is in a quantity sufficient to produce a final concentration of about 5 mM sucralose to about 10 mM sucralose in the blood sample. In some embodiments, the treated blood sample has a sucralose concentration of about 24 mM. In some embodiments, the treated blood sample has a sucralose concentration of about 25 mM. In some embodiments, the sucralose is a powder. In some embodiments, the sucralose is a solid. In some embodiments, the sucralose is lyophilized. In some embodiments, the sucralose is in solution. In some embodiments, the sucralose solution is an aqueous solution. In some embodiments, the blood collection tube is an evacuated blood collection tube. In some embodiments, the articles of manufacture further comprise an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid ($K_3$EDTA), di-potassium ethylenediaminetetraacetic acid ($K_2$EDTA), hirudin, and sodium polyanethol sulfonate (SPS). In some embodiments, the anticoagulant is acid citrate dextrose solution (ACD). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid ($K_3$EDTA). In some embodiments, the anticoagulant is di-potassium ethylenediaminetetraacetic acid ($K_2$EDTA). In some embodiments, the anticoagulant is hirudin. In some embodiments, the anticoagulant is sodium polyanethol sulfonate (SPS).

Described herein, in some embodiments, are kits, comprising an article of manufacture provided herein, and a package insert.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
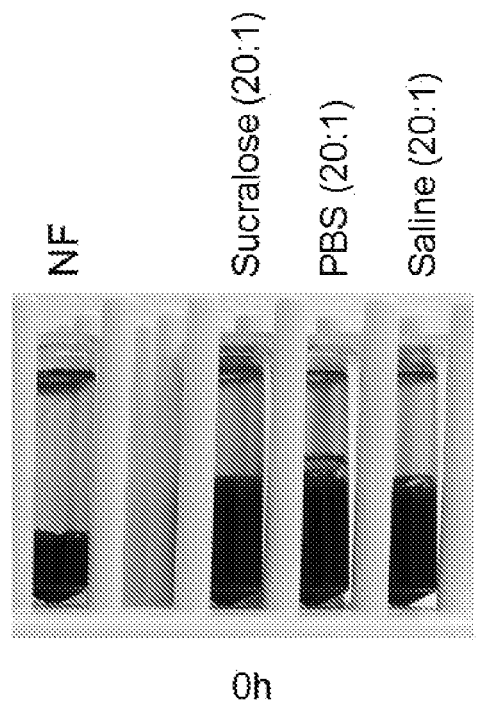
FIGS. 1A-1C illustrate reduction of erythrocyte sedimentation rate in whole blood following addition of 0.5 M sucralose, PBS, or saline. Storage was for 0 hours (FIG. 1A), 6 hours (FIG. 1B), and 24 hours (FIG. 1C). NF=no formulation control.

The present invention relates to formulations, compositions, articles of manufacture, kits, and methods for reduction of sedimentation rate of one or more erythrocytes in a blood sample.

In some embodiments, the formulations, methods, and compositions provided herein provide for reduced sedimentation rate and thus storage of the one or more erythrocytes in a blood sample at the injection site of a microfluidic device. Reduction of sedimentation rate of one or more erythrocytes in a blood sample allows for the slow injection of one or more erythrocytes into the microinjection device without the need for prior sample mixing.

Erythrocyte sedimentation rate is used as a parameter for prognosis of diseases such as multiple myeloma, temporal arteritis, polymyalgia rheumatica, systemic lupus erythematosus, and rheumatoid arthritis. Thus, in some embodiments, the formulations, methods, and compositions for reduction of erythrocyte sedimentation rate in a blood sample provided herein may benefit patients with diseases that correlate with an increased rate of erythrocyte sedimentation.

Definitions

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of ±20%, or ±10%, or ±5%, or even ±1% from the specified value, as such variations are appropriate for the disclosed compositions or to perform the disclosed methods.

Unless defined otherwise, all technical and scientific terms used herein have the same meaning as is commonly understood by one of skill in the art to which this invention belongs.

The term "ambient temperature" as used herein refers to common indoor room temperatures. In some embodiments, ambient temperature is 15 to 32° C. In some embodiments, ambient temperature is 20 to 27° C.

As used herein, the terms "reduced sedimentation rate," "reducing sedimentation rate," and "reduction of sedimentation rate," refer to the ability of a material to decrease the sedimentation rate of erythrocytes in a blood sample. In some embodiments, erythrocyte sedimentation rate is reduced by at least 10%, at least 20%, at least 30%, at least 40%, at least 50%, at least 60%, at least 70%, at least 80%, at least 90%, at least 95% of the erythrocyte sedimentation rate of the untreated blood sample. In some embodiments, reduction of sedimentation rate refers to the ability of a material to prevent one or more erythrocytes in a blood sample from settling out of suspension due to the force of gravity. In some embodiments, one or more erythrocytes are maintained in suspension for at least 30 minutes. In some embodiments, at least 10%, at least 20%, at least 30%, at least 40%, at least 50%, at least 60%, at least 70%, at least 80%, at least 90%, at least 95% of one or more erythrocytes remain in suspension in the treated blood sample as compared to the untreated blood sample. In some embodiments, one or more erythrocytes remain in suspension for at least 10 minutes, at least 20 minutes, at least 30 minutes, at least 40 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 10 hours, at least 12 hours, at least 24 hours or at least 48 hours.

Formulation Reagents
pH Buffers

According to certain embodiments, the herein described formulations and compositions for the reduction of sedimentation rate of one or more erythrocytes in a blood sample include one or more pH buffers. In some embodiments, the pH buffer is any of a large number of compounds known in the art for their ability to resist changes in the pH of a solution, such as in an aqueous solution in which the pH buffer is present. Selection of one or more particular pH buffers for inclusion in a stable storage composition may be done based on the present disclosure and according to routine practices in the art, and may be influenced by a variety of factors including the pH that is desired to be maintained, the nature of the biological sample, the solvent conditions to be employed, the other components of the formulation to be used, and other criteria. For example, typically a pH buffer is employed at a pH that is within about 0.1, 0.2, 0.3, 0.4, 0.5, 0.6, 0.7, 0.8, 0.9 or 1.0 pH unit of a proton dissociation constant ($pK_a$) that is a characteristic of the buffer.

Non-limiting examples of pH buffers include citric acid, tartaric acid, malic acid, sulfosalicylic acid, sulfoisophthalic acid, oxalic acid, borate, CAPS (3-(cyclohexylamino)-1-propanesulfonic acid), CAPSO (3-(cyclohexylamino)-2-hydroxy-1-propanesulfonic acid), EPPS (4-(2-hydroxyethyl)-1-piperazinepropanesulfonic acid), HEPES (4-(2-hydroxyethyl)piperazine-1-ethanesulfonic acid), MES (2-(N-morpholino)ethanesulfonic acid), MOPS (3-(N-morpholino) propanesulfonic acid), MOPSO (3-morpholino-2-hydroxypropanesulfonic acid), PIPES (1,4-piperazinediethanesulfonic acid), TAPS (N-[tris(hydroxymethyl)methyl]-3-aminopropanesulfonic acid), TAPSO (2-hydroxy-3-[tris(hydroxymethyl)methylamino]-1-propanesulfonic acid), TES (N-[tris(hydroxymethyl)methyl]-2-aminoethanesulfonic acid), bicine (N,N-bis(2-hydroxyethyl)glycine), tricine (N-[tris(hydroxymethyl)methyl]glycine), tris (tris(hydroxymethyl)aminomethane) and bis-tris (2-[bis(2-hydroxyethyl)amino]-2-(hydroxymethyl)-1,3-propanediol). In some embodiments, the formulations have a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

Disaccharide Derivatives

In certain embodiments, the formulations or compositions for reduction of sedimentation rate of erythrocytes in a blood sample include at least one halogenated disaccharide derivative. In some embodiments, the halogenated disaccharide derivative is a di- or tri-chlorinated disaccharide. In some embodiments, such di- or tri-chlorinated disaccharides unexpectedly are capable of reducing sedimentation rate of erythrocytes in a blood sample either alone or in the presence of only a buffer. Halogenated disaccharide derivatives are known, e.g., see US Patent Publication No. 2014/0065062, and include sucralose (1,6-dichloro-1,6-dideoxy-β-D-fructofuranosyl-4-chloro-4-deoxy-α-D-galactopyranoside), trichloronated maltose, 1,6-dichloro-1,6-dideoxy-β-D-fructofuranosyl-4-chloro-4-deoxy-6-O-monododecanoate-α-D-galactopyranoside, and 1,6-dichloro-1,6-dideoxy-β-D-fructofuranosyl-4-chloro-4-deoxy-6-O-monotetradecanoate-α-D-galactopyranoside. Selection of one or more particular halogenated disaccharide derivative for inclusion in a formulation or composition for reduction of sedimentation rate of erythrocytes in a blood sample may be done based on the present disclosure and according to routine practices in the art, and may be influenced by a variety of factors including other formulation components.

In some embodiments, the halogenated disaccharide derivative is sucralose. In some embodiments, the sucralose is provided in solution as a formulation for mixing with a blood sample. In some embodiments, the solution is an aqueous solution. In some embodiments, the sucralose is present in the formulation at about 5-500 mM. In some embodiments, the sucralose is present in the formulation at about 10-500 mM. In some embodiments, the sucralose is present in the formulation at about 50-500 mM. In some embodiments, the sucralose is present in the formulation at about 100-500 mM. In some embodiments, the sucralose is present in the formulation at about 250-500 mM. In some embodiments, the sucralose is present in the formulation at about 5-630 mM. In some embodiments, the sucralose is present in the formulation at about 5-750 mM. In some embodiments, the sucralose is present in the formulation at about 10-750 mM. In some embodiments, the sucralose is present in the formulation at about 50-750 mM. In some embodiments, the sucralose is present in the formulation at about 100-750 mM. In some embodiments, the sucralose is present in the formulation at about 250-750 mM. In some embodiments, the formulation is a mixture of water and sucralose.

In some embodiments, the formulation is provided in an amount sufficient to produce a final concentration of sucralose of about 5 to about 25 mM, when mixed with a blood sample. In some embodiments, the sucralose is present in the formulation at about 500 mM and is mixed with a blood sample at a ratio of 1:20 (v/v) (formulation to blood). In some embodiments, the sucralose is present in the formulation at greater than 25 mM up to 100 mM. In some embodiments, the sucralose is present in the formulation at about 13-24 mM. In some embodiments, the sucralose is provided in powder form as a formulation for mixing with a blood sample. In some embodiments, the sucralose powder is provided in an amount sufficient to produce a final concentration of sucralose of about 5 to about 25 mM, when mixed with a blood sample.

In some embodiments, the sucralose is present at a final concentration of about 5-100 mM, when mixed with a blood sample. In some embodiments, the sucralose is present at a final concentration of about 5-50 mM, when mixed with a blood sample. In some embodiments, the sucralose is present at a final concentration of about 5-25 mM, when mixed with a blood sample. In some embodiments, the sucralose is present at a final concentration of about 5 up to but not including 25 mM, when mixed with a blood sample. In some embodiments, the sucralose is present at a final concentration of about 5-20 mM, when mixed with a blood sample. In some embodiments, the sucralose is present at a final concentration of about 5-15 mM, when mixed with a blood sample. In some embodiments, the sucralose is present at a final concentration of about 10-20 mM, when mixed with a blood sample. In some embodiments, the sucralose is present at a final concentration of about 10-15 mM, when mixed with a blood sample. In some embodiments, the sucralose is present at a final concentration of about 5-10 mM, when mixed with a blood sample. In some embodiments, the sucralose and is present at a final concentration of about 25 mM, when mixed with a blood sample.

Anticoagulants

In some embodiments, an anticoagulant is included in the presently described formulations and compositions. Such anticoagulants are known in the art. Exemplary anticoagulants include acid citrate dextrose solution (ACD), ethylenediaminetetraacetic acid (EDTA), tri-potassium ethylenediaminetetraacetic acid (K$_3$EDTA), di-potassium ethylenediaminetetraacetic acid (K$_2$EDTA), heparin, sodium heparin, sodium fluoride, lithium heparin, sodium citrate, hirudin, and sodium polyanethol sulfonate (SPS). In some embodiments, the anticoagulant is contained within a blood collection tube.

Exemplary Formulations for Reduction of Erythrocyte Sedimentation Rate in a Blood Sample Described herein, in some embodiments, are formulations comprising sucralose. In some embodiments, the sucralose is present at a final concentration of about 5 mM sucralose to about 50 mM sucralose, when mixed with a blood sample. In some embodiments, the sucralose is present at a final concentration of about 5 mM sucralose to about 25 mM sucralose, when mixed with a blood sample. In some embodiments, the sucralose is present at a final concentration of about 5 mM sucralose up to, but not including, 25 mM sucralose. In some embodiments, the sucralose is present at a final concentration of about 5 mM sucralose to about 20 mM sucralose. In some embodiments, the sucralose is present at a final concentration of about 5 mM sucralose to about 15 mM sucralose. In some embodiments, the sucralose is present at a final concentration of about 5 mM sucralose to about 10 mM sucralose. In some embodiments, the sucralose is present as a solution. In some embodiments, the solution is an aqueous solution. In some embodiments, the sucralose is present as a powder. In some embodiments, the formulations further comprise an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid (K$_3$EDTA), di-potassium ethylenediaminetetraacetic acid (K$_2$EDTA), hirudin, and sodium polyanethol sulfonate (SPS). In some embodiments, the anticoagulant is acid citrate dextrose solution (ACD). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid (K$_3$EDTA). In some embodiments, the anticoagulant is di-potassium ethylenediaminetetraacetic acid (K$_2$EDTA). In some embodiments, the anticoagulant is hirudin. In some embodiments, the anticoagulant is sodium polyanethol sulfonate (SPS). In some embodiments, the formulation is contained within a blood collection tube.

Methods for Preparing Formulations for Reducing Erythrocyte Sedimentation Rate in a Blood Sample Methods for preparing the formulations described herein for reduction of erythrocyte sedimentation rate in a blood sample employ techniques that are well-known to those skilled in the art and generally use commercially available reagents. In some embodiments, the formulations are prepared as concentrated stock solutions of the formulation reagents, e.g., 2×, 5×, 10×, 20× or the like, so as to be admixed with the blood sample at the appropriate ratios to produce the desired final concentrations of sucralose in the blood sample.

Compositions of Erythrocytes in a Blood Sample with Reduced Sedimentation Rate

Described herein, in some embodiments, are compositions comprising a blood sample and sucralose, wherein the sucralose is at a concentration of about 5 mM sucralose up to, but not including, about 25 mM sucralose. In some embodiments, the compositions further comprise an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid (K$_3$EDTA), di-potassium ethylenediaminetetraacetic acid (K$_2$EDTA), hirudin, and sodium polyanethol sulfonate (SPS). In some embodiments, the anticoagulant is acid citrate dextrose solution (ACD). In some embodiments, the anticoagulant is acid citrate dextrose solution A (ACD-A). In some embodiments, the anticoagulant is acid citrate dextrose solution B (ACD-B). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid (K$_3$EDTA). In some embodiments, the anticoagulant is di-potassium ethylenediaminetetraacetic acid (K$_2$EDTA). In some embodiments, the anticoagulant is hirudin. In some embodiments, the anticoagulant is sodium polyanethol sulfonate (SPS). In some embodiments, the composition is contained within a blood collection tube. In some embodiments, the blood collection tube is an evacuated blood collection tube. In some embodiments, the blood is collected from a subject. In some embodiments, the subject is a mammal. In some embodiments, the subject is a human. In some embodiments, the compositions of one or more erythrocytes in a blood sample with reduced sedimentation rate are stored in the formulations described herein for extended periods of time before analysis in, for example, a microfluidic device.

Articles of Manufacture

In certain embodiments, articles of manufacture are provided, which comprise a formulation provided herein, contained within a suitable blood collection tube, container or vessel for collection of a biological sample. In some embodiments, these articles of manufacture are used for reducing sedimentation rate of one or more erythrocytes in a blood sample at the time of biological sample collection. In certain embodiments, the blood collection tube is an evacuated blood tube having less than atmospheric pressure to withdraw a predetermined volume of whole blood. In some embodiments, the blood collection tube contains about 28.6 mg of sucralose powder and the blood collection tube is of a size to contain a blood draw volume of 3.0 mL blood to produce a final sucralose concentration of about 24 mM after the addition of 3.0 mL blood. In some embodiments, the blood collection tube contains about 33.4 mg of sucralose powder and the blood collection tube is of a size to contain a blood draw volume of 3.5 mL blood. In some embodiments, the blood collection tube contains about 42.9 mg of sucralose powder and the blood collection tube is of a size to contain a blood draw volume of 4.5 mL blood. In some embodiments, the blood collection tube contains about 52.4 mg of sucralose powder and the blood collection tube is of a size to contain a blood draw volume of 5.5 mL blood. In some embodiments, the blood collection tube contains about 95.4 mg of sucralose powder and the blood collection tube is of a size to contain a blood draw volume of 10 mL blood. In some embodiments, these articles of manufacture are used in the kits and methods described herein.

Kits

In certain embodiments, there are provided kits comprising any one of the articles of manufacture described herein and a package insert. In some embodiments, the components of the kit are supplied in a container. In some embodiments, the container is a compartmentalized plastic enclosure. In some embodiments, the container includes a hermetically sealable cover so that the contents of the kit can be sterilized and sealed for storage.

Methods for Reducing Sedimentation Rate of Erythrocytes in a Blood Sample

Described herein, in some embodiments, are in vitro methods for reducing the erythrocyte sedimentation rate in a blood sample, comprising: combining a sample of blood with an amount of a formulation comprising sucralose, wherein the amount is sufficient to produce a treated blood sample having a sucralose concentration of at least about 5 mM sucralose, thereby reducing the erythrocyte sedimentation rate as compared to erythrocyte sedimentation rate in an untreated blood sample. In some embodiments, the treated blood sample has a sucralose concentration of about 5 mM sucralose to about 50 mM sucralose. In some embodiments, the treated blood sample has a sucralose concentration of about 5 mM sucralose to about 25 mM sucralose. In some embodiments, the treated blood sample has a sucralose concentration of about 5 mM sucralose up to but not including 25 mM sucralose. In some embodiments, erythrocyte sedimentation rate is reduced by at least 10%, at least 20%, at least 30%, at least 40%, at least 50%, at least 60%, at least 70%, at least 80%, at least 90%, at least 95% of the erythrocyte sedimentation rate of the untreated blood sample. In some embodiments, the formulation is a powder. In some embodiments, the formulation is a solution. In some embodiments, the solution is an aqueous solution. In some embodiments, the formulation consists of sucralose. In some embodiments, the formulation further comprises an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid ($K_3EDTA$), di-potassium ethylenediaminetetraacetic acid ($K_2EDTA$), hirudin, and sodium polyanethol sulfonate (SPS). In some embodiments, the anticoagulant is acid citrate dextrose solution (ACD). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid ($K_3EDTA$). In some embodiments, the anticoagulant is di-potassium ethylenediaminetetraacetic acid ($K_2EDTA$). In some embodiments, the anticoagulant is hirudin. In some embodiments, the anticoagulant is sodium polyanethol sulfonate (SPS). In some embodiments, the formulation is contained within a blood collection tube, and the combining step occurs within the blood collection tube. In some embodiments, the blood collection tube is an evacuated blood collection tube. In some embodiments, the blood is collected from a subject. In some embodiments, the subject is a mammal. In some embodiments, the subject is a human.

Described herein, in some embodiments, are methods for maintaining one or more erythrocytes in suspension in a blood sample, comprising: combining a sample of blood with an amount of a formulation comprising sucralose, wherein the amount is sufficient to produce a treated blood sample having a sucralose concentration of at least about 5 mM sucralose, thereby maintaining the one or more erythrocytes in suspension for a period of at least 30 minutes as compared to an untreated blood sample. In some embodiments, the one or more erythrocytes remain in suspension for a period of at least 10 minutes, at least 20 minutes, at least 30 minutes, at least 40 minutes, at least 50 minutes, at least 1 hour, at least 2 hours, at least 3 hours, at least 4 hours, at least 5 hours, at least 6 hours, at least 7 hours, at least 8 hours, at least 10 hours, at least 12 hours, at least 24 hours or at least 48 hours. In some embodiments, the treated blood sample has a sucralose concentration of about 5 mM sucralose to about 25 mM sucralose. In some embodiments, the treated blood sample has a sucralose concentration of about 5 mM sucralose up to but not including 25 mM sucralose. In some embodiments, at least 10%, at least 20%, at least 30%, at least 40%, at least 50%, at least 60%, at least 70%, at least 80%, at least 90%, at least 95% of the one or more erythrocytes remain in suspension in the treated blood sample as compared to the untreated blood sample. In some embodiments, the formulation is a powder. In some embodiments, the formulation is a solution. In some embodiments, the solution is an aqueous solution. In some embodiments, the formulation consists of sucralose. In some embodiments, the formulation further comprises an anticoagulant. In some embodiments, the anticoagulant is selected from the group consisting of acid citrate dextrose solution (ACD), sodium heparin, sodium fluoride, lithium heparin, tri-potassium ethylenediaminetetraacetic acid ($K_3EDTA$), di-potassium ethylenediaminetetraacetic acid ($K_2EDTA$), hirudin, and sodium polyanethol sulfonate (SPS). In some embodiments, the anticoagulant is acid citrate dextrose solution (ACD). In some embodiments, the anticoagulant is sodium heparin. In some embodiments, the anticoagulant is sodium fluoride. In some embodiments, the anticoagulant is lithium heparin. In some embodiments, the anticoagulant is tri-potassium ethylenediaminetetraacetic acid ($K_3EDTA$). In some embodiments, the anticoagulant is di-potassium ethylenediaminetetraacetic acid ($K_2EDTA$). In some embodiments, the anticoagulant is hirudin. In some embodiments, the anticoagulant is sodium polyanethol sulfonate (SPS). In some embodiments, the formulation is contained within a blood collection tube, and the combining step occurs within the blood collection tube. In some embodiments, the blood collection tube is an evacuated blood collection tube. In some embodiments, the blood sample is collected from a subject. In some embodiments, the subject is a mammal. In some embodiments, the subject is a human.

Blood collection tubes, bags, containers and vessels are well-known in the art and have been employed by medical practitioners for decades. Blood collected for reduction of erythrocyte sedimentation rate may be obtained using any method or apparatus commonly employed by those skilled in the art such as venipuncture or finger prick. In some embodiments, when the blood is collected by venipuncture, the formulation is located inside the blood collection tube, e.g., an evacuated tube (VACUTAINER® blood collection tube, Becton Dickinson or VACUETTE® blood collection tube, Greiner Bio-One) at the time that the blood sample is obtained from the subject. In some embodiments, when the blood is collected by venipuncture, the formulations are added to an already obtained whole blood sample, either immediately or shortly after it is withdrawn.

In some embodiments, the methods as described herein use the articles of manufacture and kits disclosed.

The following Examples are presented by way of illustration and not limitation.

Example 1

Reduction of Erythrocyte Sedimentation Rate in Whole Blood by Addition of Sucralose This Example describes reduction of erythrocyte sedimentation in whole blood by addition of sucralose.

Fresh blood was collected into BD $K_2EDTA$ VACUTAINER® tubes and pooled. Blood and a solution of 0.5 M sucralose were mixed at a ratio of 20:1 by aliquotting 952 µL of fresh blood into 2 mL centrifuge tubes containing 48 µL of formulation, resulting in a concentration of about 24 mM sucralose. 48 µL of PBS and 0.9% saline served as controls. Blood with no formulation (NF) added served as an additional control. The filled centrifuge tubes were gently inverted five times to mix and stored upright on the benchtop at approximately 25° C. Tubes were photographed at 0 hours (FIG. 1A), 6 hours (FIG. 1B), and 24 hours (FIG. 1C) against a white background for visual analysis of sedimentation rate.

Figure 1B:
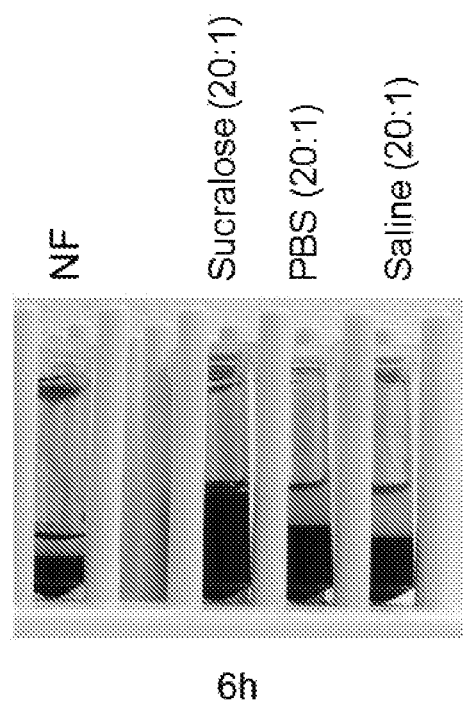
Figure 1C:
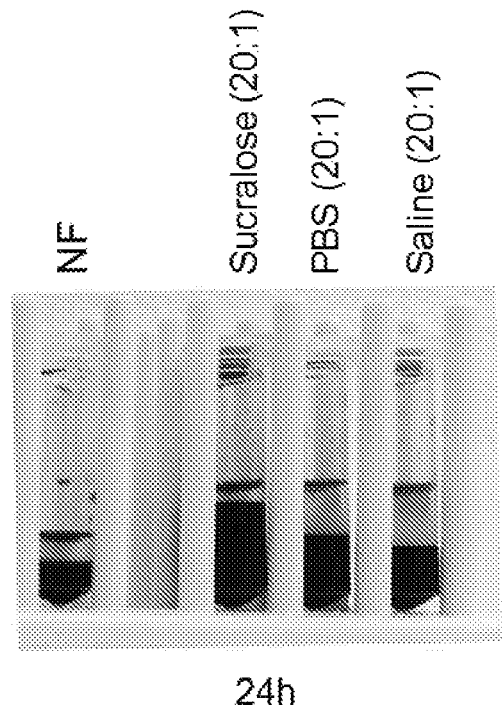

As shown in FIGS. 1A-C, whole blood collected in $K_2EDTA$ tubes containing sucralose had lower sedimentation rate of the erythrocytes after storage of the aliquots at ambient temperature for 6 hours and 24 hours compared to whole blood only (NF) or whole blood following addition of either PBS or saline.

Example 2

Effect of Sucralose Concentration and Other Saccharides on Reduction of Erythrocyte Sedimentation Rate This Example illustrates the effect on sucralose concentration and other saccharides on reduction of erythrocyte sedimentation rate in whole blood.

Figure 2:
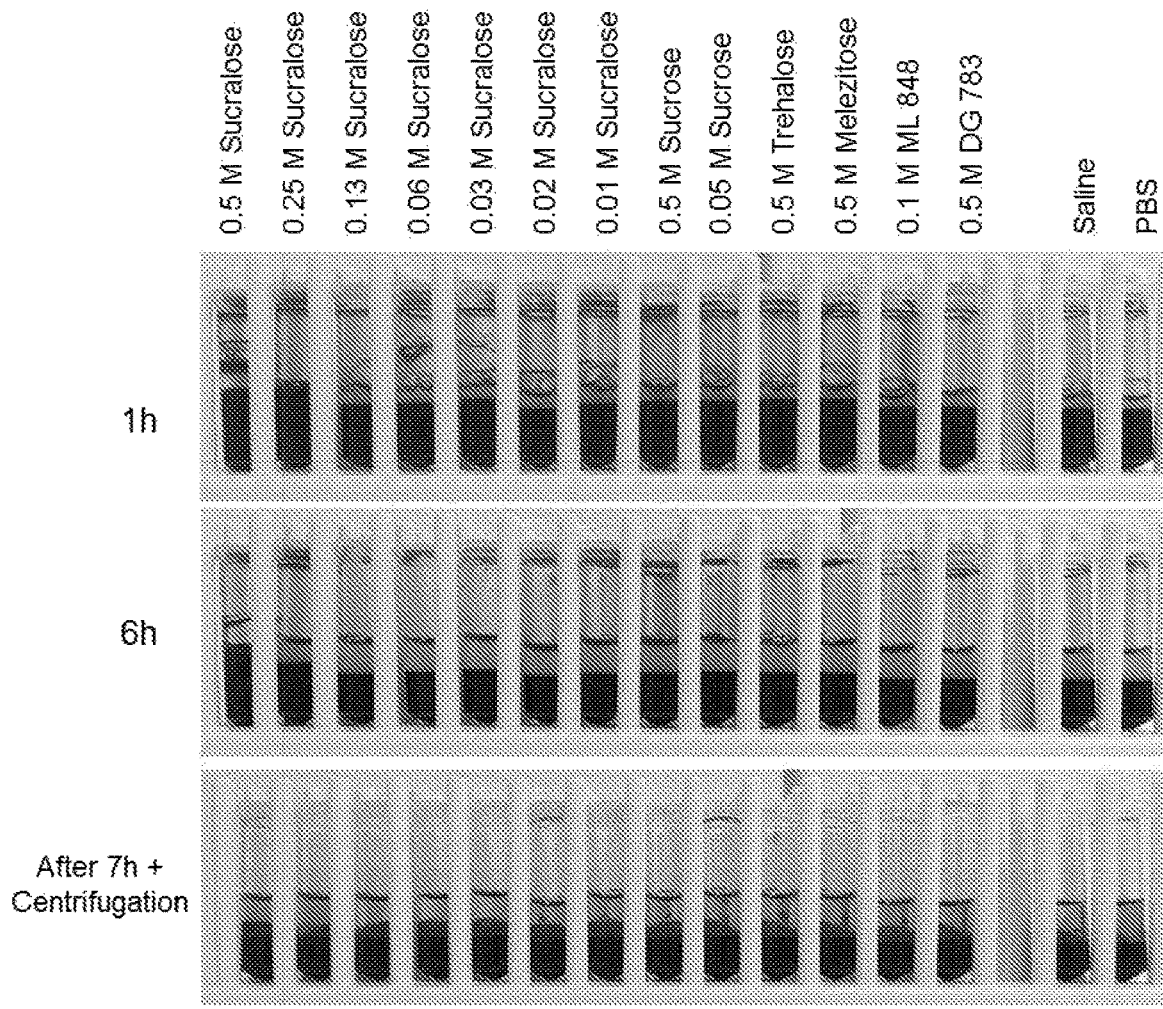
FIG. 2 illustrates sedimentation rate of erythrocytes in whole blood following addition of the indicated solution of sucralose, the indicated saccharide, PBS, or saline. Storage was for 1 hour (upper panel) and 6 hours (center panel). Lack of hemolysis from the reduction of sedimentation rate is illustrated in the bottom panel by centrifugation after 7 hours of storage.

Fresh blood was collected into BD $K_2EDTA$ VACUTAINER® tubes and pooled. 952 µL of fresh blood was aliquot into 2 mL centrifuge tubes, each containing 48 µL of sucralose at the indicated concentration in FIG. 2, or the indicated saccharide (ML848, a di-chlorinated monosaccharide, or DG783, a mono-fluorinated monosaccharide) at the indicated concentration. Sucralose solutions of different concentrations were prepared by dilution of 0.5 M sucralose to 10 mM in water. Formulations were adjusted to 300 mOsmol with NaCl, with the exception of formulations of the highest concentration that had an osmolarity of 500 mOsmol. 48 µL of PBS and 0.9% saline served as controls. Final concentrations of sucralose or the indicated saccharide shown in FIG. 2 were as follows (from left to right): 24 mM sucralose, 12 mM sucralose, 6.24 mM sucralose, 2.88 mM sucralose, 1.44 mM sucralose, 0.96 mM sucralose, 0.48 mM sucralose, 24 mM sucrose, 2.4 mM sucrose, 24 mM trehalose, 24 mM melezitose, 4.8 mM ML848, and 24 mM DG783.

The filled centrifuge tubes were gently inverted five times to mix and stored upright on the benchtop at approximately 25° C. Tubes were photographed at 1 hour (FIG. 2, upper panel) and 6 hours (FIG. 2, center panel) against a white background for visual analysis of sedimentation rate. After 7 hours of storage, tubes were centrifuged for 20 min at 3000 rpm to determine the effect of hemolysis on sedimentation rate by visual analysis (FIG. 2, lower panel).

FIG. 2 shows that whole blood collected in $K_2EDTA$ tubes containing high concentrations of sucralose had lower sedimentation rate of erythrocytes after storage of aliquots at ambient temperature for 1 hour (upper panel) and 6 hours (center panel). Lower sedimentation rate of erythrocytes was not observed in samples that had final sucralose concentrations below 5 mM, or in samples following addition of sucrose, trehalose, melezitose, ML848, DG783, PBS, or saline to whole blood.

Homogeneity of whole blood in the presence of a high concentration of sucralose was not due to excessive hemolysis of erythrocytes, as shown by centrifugation of the sample after 7 hours of storage (FIG. 2, lower panel). Centrifugation resulted in clear separation of plasma without coloration of the plasma layer similar to that seen for the saline and PBS sample controls (FIG. 2, lower panel). Significant hemolysis was not seen at final sucralose concentrations at or below 40 mM.

Example 3

Effect of Sucralose Added as a Powder on Reduction of Erythrocyte Sedimentation Rate This Example describes the effect of addition of sucralose in powder form on reduction of erythrocyte sedimentation rate in whole blood.

Fresh blood was collected into BD $K_2$EDTA VACU-TAINER® tubes and pooled. 1 mL of fresh blood was aliquotted into 2 mL centrifuge tubes containing sucralose powder. Final concentrations of sucralose ranged from 7.5 mM to 100 mM, corresponding to 3.0 mg to 39.8 mg per mL of blood. The no formulation (NF) control sample received no addition of sucralose. Tubes were inverted at least five times until no visible undissolved material remained at the bottom of the tubes. Tubes were stored upright on the benchtop at approximately 25° C. Tubes were photographed at 1 hour (FIG. 3, upper panel) and 6 hours (FIG. 3, lower panel) against a white background for visual analysis of sedimentation rate.

Figure 3:
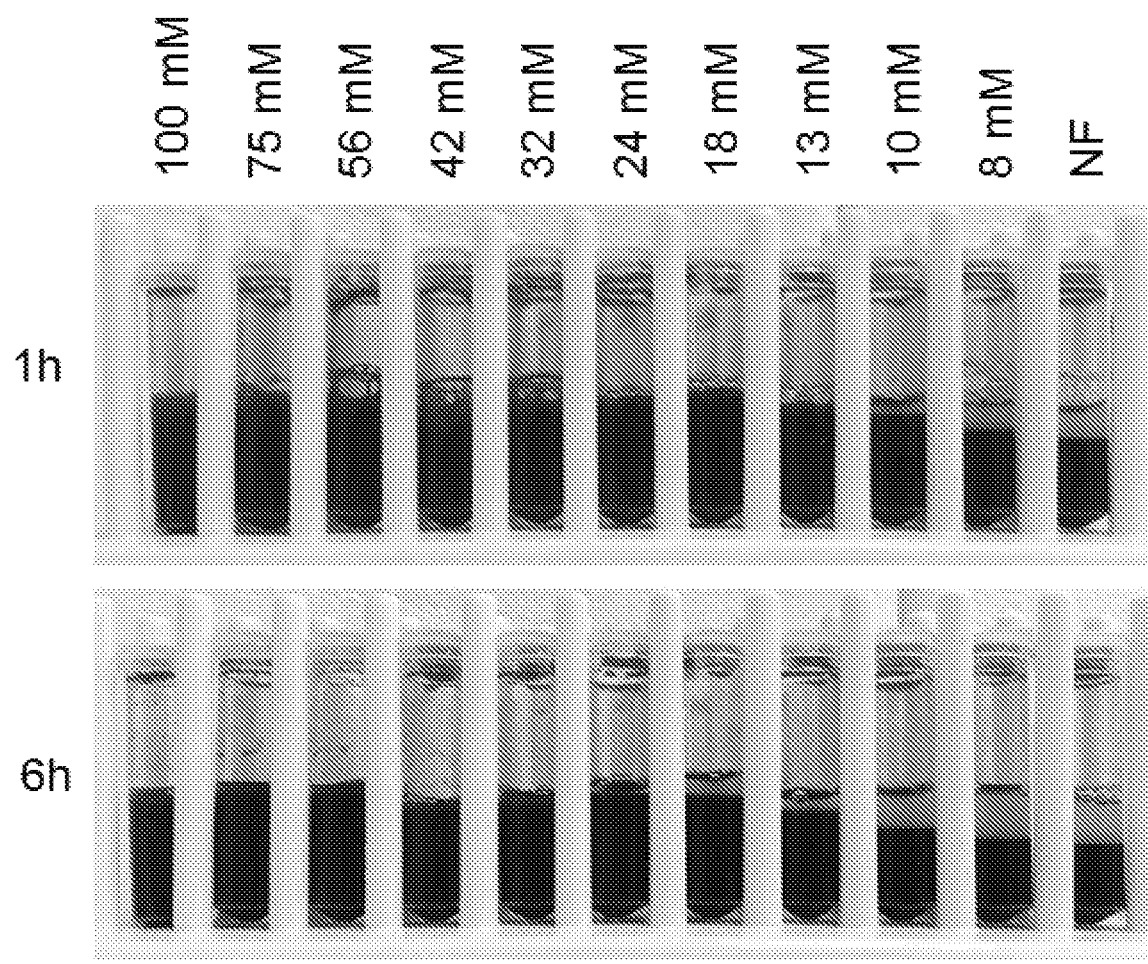
FIG. 3 illustrates sedimentation rate of erythrocytes following addition of sucralose in powder form to the indicated final concentration. Storage of samples was for 1 hour (upper panel) and 6 hours (lower panel). NF=no formulation control.

Data in FIG. 3 shows that the rate of erythrocyte sedimentation was inversely proportional to the concentration of sucralose. At a sucralose concentration of 24 mM or greater, homogeneity of whole blood samples stored at ambient temperatures for 6 hours was observed, while lower concentrations of sucralose resulted in separation of the erythrocyte and plasma layers.

Example 4

Effect of Blood Collection Conditions on Reduction of Erythrocyte Sedimentation Rate This Example describes the effect of different anticoagulants present at the time of blood collection on reduction of erythrocyte sedimentation rate in whole blood.

Figure 4:
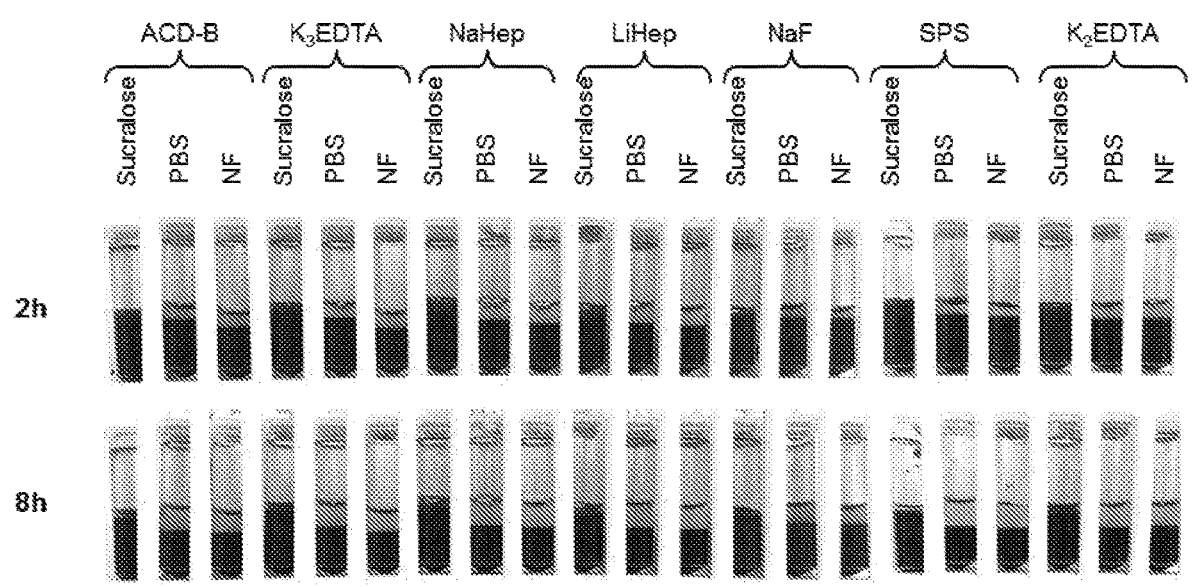
FIG. 4 illustrates the effect of different anticoagulants on sedimentation rate of erythrocytes collected from whole blood. Samples were collected into blood collection tubes containing the indicated anticoagulant. Storage of samples following addition of a solution of 0.5 M sucralose or PBS was for 2 hours (upper panel) and 8 hours (lower panel). NF=no formulation control.

To screen for collection conditions, fresh blood was collected into a series of BD VACUTAINER® or Greiner Bio-One VACUETTE® low-volume blood collection tubes containing different anticoagulants, including acid citrate dextrose solution B (ACD-B), tri-potassium ethylenediaminetetraacetic acid ($K_3$EDTA), sodium heparin (NaHep), lithium heparin (LiHep), sodium fluoride (NaF), and sodium polyanethol sulfonate (SPS). Collection into tubes containing di-potassium ethylenediaminetetraacetic acid ($K_2$EDTA) served as a control. 952 µL of fresh blood was aliquot into 2 mL centrifuge tubes containing 48 µL of 0.5 M sucralose or PBS. No formulation (NF) added served as an additional control. The filled centrifuge tubes were gently inverted five times to mix and stored upright on the benchtop at approximately 25° C. Tubes were photographed at 2 hours (FIG. 4, upper panel) and 8 hours (FIG. 4, lower panel) against a white background for visual analysis of sedimentation rate. As shown in FIG. 4, addition of 0.5 M sucralose, for a final sucralose concentration of 24 mM in the treated sample, resulted in reduction of erythrocyte sedimentation rate for each anticoagulant present in the blood collection tube at the time of blood collection. By contrast, addition of PBS had no effect on erythrocyte sedimentation rate.

Example 5

Effect of Sucralose Compared to Polyols and Halogenated Polyols on Reduction of Erythrocyte Sedimentation Rate This Example describes the effect of sucralose compared to the effect of polyols and halogenated polyols on reduction of erythrocyte sedimentation rate in whole blood.

Fresh blood was collected into BD $K_2$EDTA VACU-TAINER® tubes and pooled. 952 µL of fresh blood was aliquot into 2 mL centrifuge tubes containing 48 µL of a solution of 0.5 M sucralose, the indicated polyol, or the indicated halogenated polyol. Additives at 0.25 M were adjusted to 300 mOsmol with NaCl. PBS and no formulation (NF) added served as controls. The filled centrifuge tubes were gently inverted five times to mix and stored upright on the benchtop at approximately 25° C. Tubes were photographed at 2 hours against a white background for visual analysis of sedimentation rate.

Figure 5:
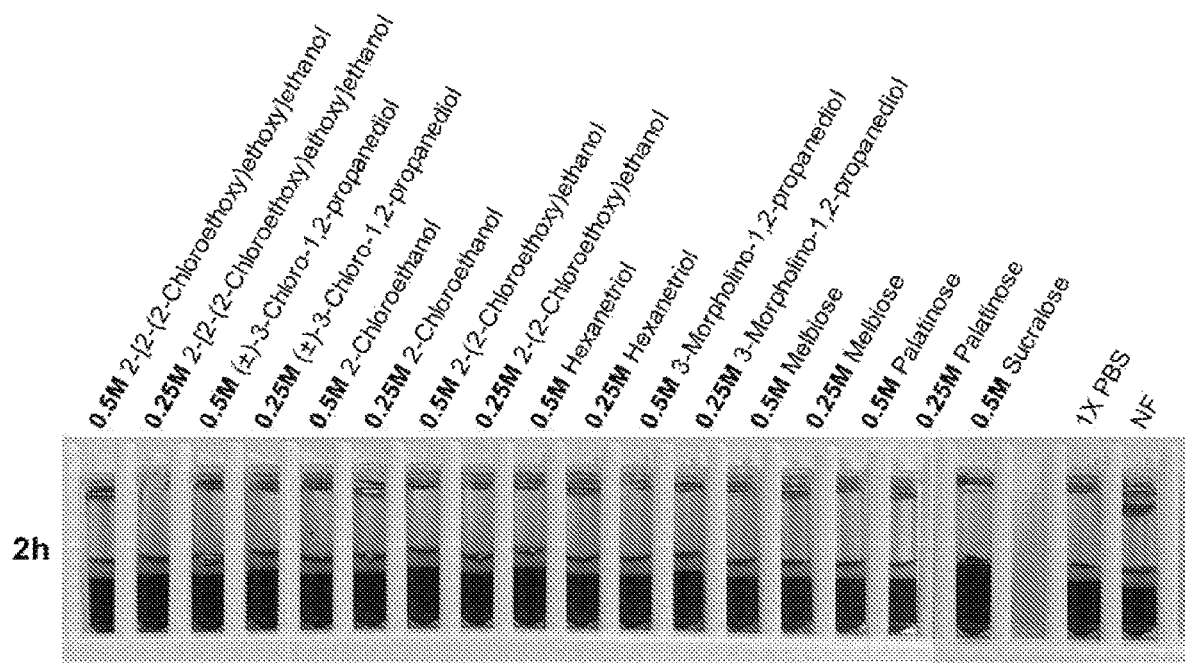
FIG. 5 illustrates the effect of a solution of 0.5 M sucralose on sedimentation rate of erythrocytes in whole blood compared to PBS, the indicated polyols, and the indicated halogenated polyols. Storage of samples was for 2 hours. NF=no formulation control.

Data in FIG. 5 shows that addition of a solution of 0.5 M sucralose, for a final sucralose concentration of 24 mM in the treated sample, resulted in reduced erythrocyte sedimentation rate. By contrast, addition of indicated polyols or halogenated polyols had no apparent effect on erythrocyte sedimentation.

Unless the context requires otherwise, throughout the present specification and claims, the word "comprise" and variations thereof, such as, "comprises" and "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An in vitro method for reducing the erythrocyte sedimentation rate in a blood sample, comprising: combining a sample of blood with an amount of a formulation comprising sucralose sufficient to produce a treated blood sample having a sucralose concentration of about 5 mM to about 50 mM sucralose, thereby reducing the erythrocyte sedimentation rate as compared to erythrocyte sedimentation rate in an untreated blood sample.

2. The method of claim 1, wherein the treated blood sample has a sucralose concentration of about 5 mM up to 25 mM sucralose.

3. The method of any one of claim 1, wherein erythrocyte sedimentation rate is reduced by at least 10%, at least 20%, at least 30%, at least 40%, at least 50%, at least 60%, at least 70%, at least 80%, at least 90%, at least 95% of the erythrocyte sedimentation rate of the untreated blood sample.

4. The method of claim 1, wherein the formulation is in the form of a powder, a solid, a lyophilized form, a solution, or an aqueous solution.

5. The method of any one of claim 1, wherein the formulation consists of sucralose.

6. The method of claim 1, wherein the formulation further comprises an anticoagulant.

7. The method of claim 6, wherein the anticoagulant is selected from the group consisting of acid citrate dextrose solution (ACD), sodium heparin, sodium fluoride, lithium heparin, tri-potassium ethylenediaminetetraacetic acid (K3EDTA), di-potassium ethylenediaminetetraacetic acid (K2EDTA), hirudin, and sodium polyanethol sulfonate (SPS).

8. The method of any one of claim 1, wherein the formulation is contained within a blood collection tube, and the combining step occurs within the blood collection tube.

9. The method of claim 8, wherein the blood collection tube is an evacuated blood collection tube.

10. The method of claim 1, wherein one or more erythrocytes of the treated blood sample are maintained in suspension for a period of at least 30 minutes as compared to an untreated blood sample.

11. A composition comprising a blood sample and sucralose, wherein the sucralose is at a concentration of about 5 mM sucralose up to but not including 50 mM sucralose.

12. The composition of claim 11, wherein the sucralose is at a concentration of about 5 mM sucralose up to but not including 25 mM sucralose.

13. The composition of claim 11, further comprising an anticoagulant.

14. The composition of claim 13, wherein the anticoagulant is selected from the group consisting of acid citrate dextrose solution (ACD), sodium heparin, sodium fluoride, lithium heparin, tri-potassium ethylenediaminetetraacetic acid (K3EDTA), di-potassium ethylenediaminetetraacetic acid (K2EDTA), hirudin, and sodium polyanethol sulfonate (SPS).

15. The composition of claim 11, wherein the blood is human.

* * * * *